(12) United States Patent
Saruya

(10) Patent No.: US 7,128,709 B2
(45) Date of Patent: Oct. 31, 2006

(54) ENDOSCOPE APPARATUS

(75) Inventor: Nobuyuki Saruya, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 328 days.

(21) Appl. No.: 10/658,548

(22) Filed: Sep. 10, 2003

(65) Prior Publication Data

US 2004/0171913 A1 Sep. 2, 2004

(30) Foreign Application Priority Data

Sep. 11, 2002 (JP) .............................. 2002-265724

(51) Int. Cl.
*A61B 1/01* (2006.01)
(52) U.S. Cl. ...................... 600/132; 600/130; 600/146
(58) Field of Classification Search ................ 600/101, 600/102, 132, 131, 130, 109, 146
See application file for complete search history.

(56) References Cited

U.S. PATENT DOCUMENTS

| 4,432,604 | A | * | 2/1984 | Schwab | ........................ 385/60 |
|---|---|---|---|---|---|
| 4,539,586 | A | * | 9/1985 | Danna et al. | .................. 348/75 |
| 4,708,126 | A | | 11/1987 | Toda | |
| 5,313,936 | A | | 5/1994 | Miyazaki et al. | |
| 5,701,155 | A | | 12/1997 | Wood et al. | |
| 5,967,969 | A | * | 10/1999 | Enomoto et al. | ............ 600/117 |
| 6,295,082 | B1 | * | 9/2001 | Dowdy et al. | ................. 348/72 |
| 6,315,712 | B1 | * | 11/2001 | Rovegno | .................... 600/109 |
| 6,348,035 | B1 | * | 2/2002 | Takami | ........................ 600/132 |
| 6,652,451 | B1 | * | 11/2003 | Murata et al. | .............. 600/118 |
| 2004/0133075 | A1 | * | 7/2004 | Motoki et al. | .............. 600/131 |
| 2004/0158128 | A1 | * | 8/2004 | Fujikawa et al. | ............ 600/132 |

FOREIGN PATENT DOCUMENTS

JP 7-181400 7/1995

* cited by examiner

*Primary Examiner*—John P. Leubecker
(74) *Attorney, Agent, or Firm*—Dickstein, Shapiro, LLP.

(57) ABSTRACT

An endoscope apparatus includes at least one of a connector on the side of a scope unit and a connector on the side of a fixed unit in a connector portion disposed in an detachable portion of a base unit and the fixed unit of the scope unit is a movable connector, and in the detachable portion, the base unit is connected to the fixed unit by positioning means for positioning the fixed unit side to the base unit side, when the connector on the fixed unit side is connected to that on the base unit side.

16 Claims, 28 Drawing Sheets

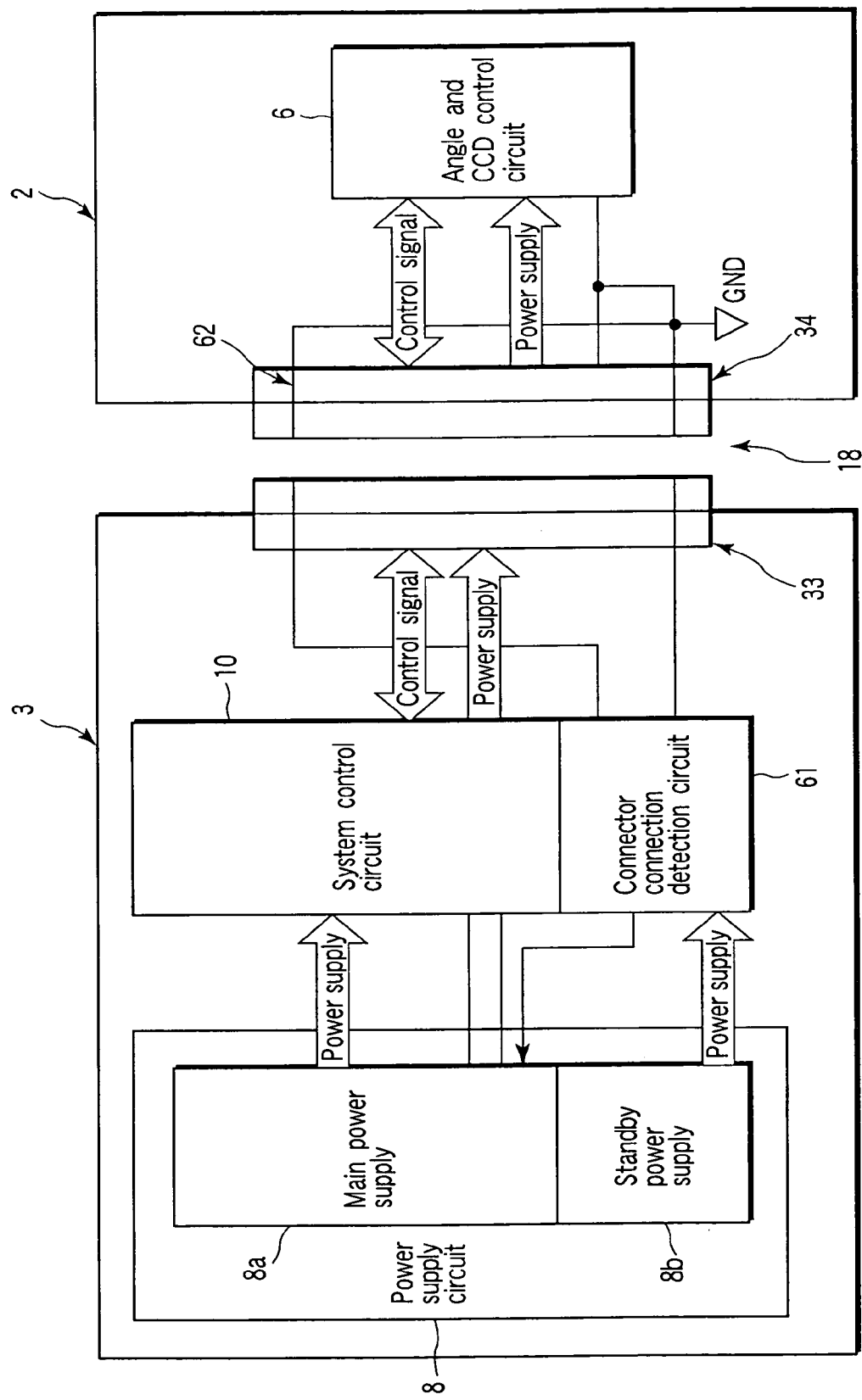
F I G. 16

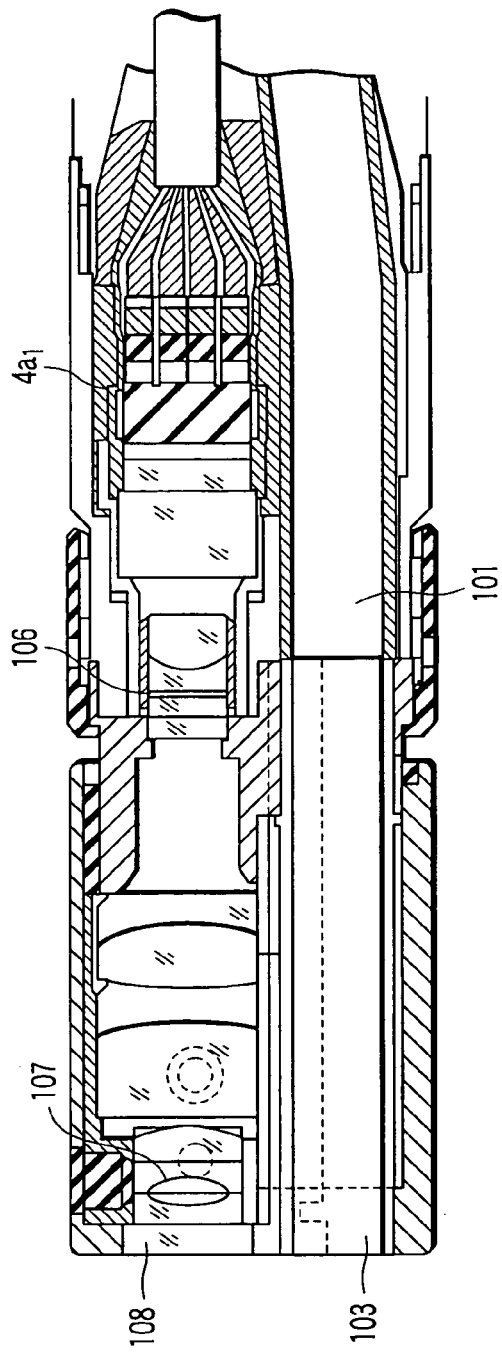
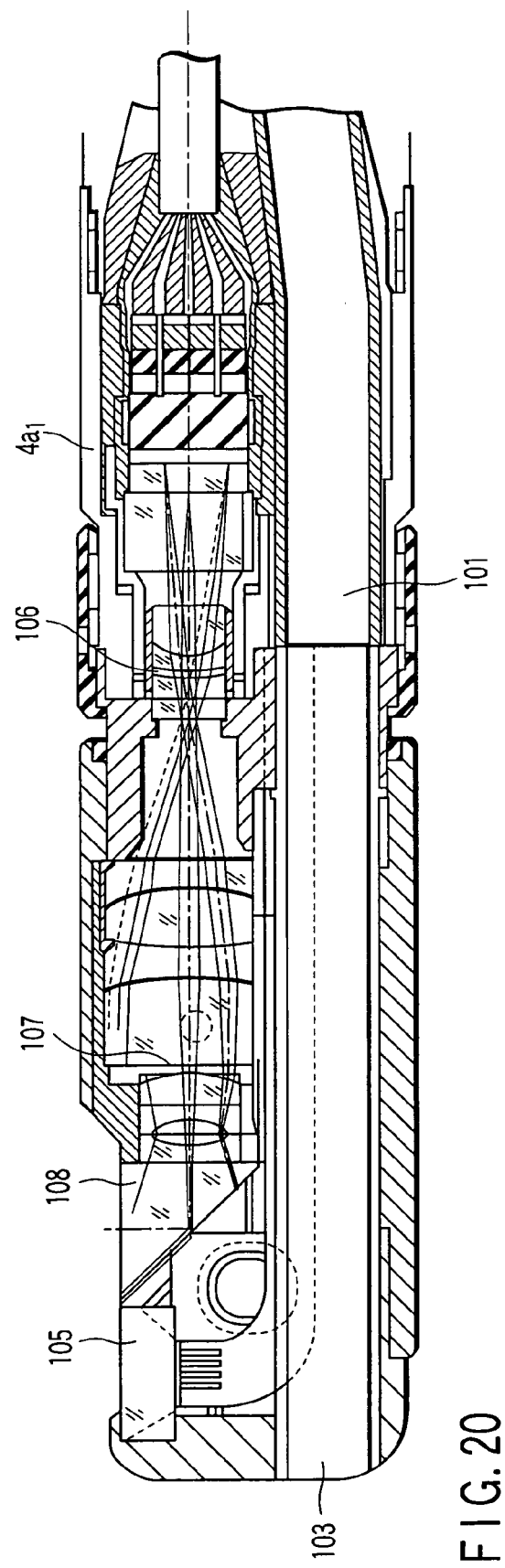
FIG. 19
FIG. 20

ENDOSCOPE APPARATUS

CROSS-REFERENCE TO RELATED APPLICATIONS

This application is based upon and claims the benefit of priority from prior Japanese Patent Application No. 2002-265724, filed Sep. 11, 2002, the entire contents of which are incorporated herein by reference.

BACKGROUND OF THE INVENTION

The present invention relates to an endoscope apparatus which is used in an industrial field and which is inserted into an inspection object space such as a pipe to observe the inside of the inspection object space, and the like.

As a general endoscope apparatus, a constitution described, for example, in Jpn. Pat. Appln. KOKAI Publication No. 7-181400 is known. In this publication, an operation portion on a hand side is connected to a base end of an elongated insertion portion inserted into the inspection object space. Furthermore, an observation optical system including an image pickup device for observation, an illuminating window for irradiation with an illuminative light, and the like are disposed in a tip end of the insertion portion.

Moreover, the operation portion is connected to one end of a universal cable. This universal cable includes a light guide for transmitting the illuminative light, a signal line for transmitting a signal output from the image pickup device, and the like. The other end of the universal cable is connected to a connector portion.

The connector portion is detachably connected to an external apparatus including a light source apparatus or a camera control unit (CCU). An elastically supported socket is disposed in the light source apparatus. The connector portion of the universal cable is inserted and connected into the socket, and in this state a connected portion of the connector portion and the socket is elastically supported.

Furthermore, a fixed unit which is usable in common in a plurality of types of endoscope apparatuses is disposed. Some of members of an external peripheral apparatus are mounted on the fixed unit. A system is proposed in which the fixed unit is combined and used with a plurality of types of scope units of the endoscope apparatus.

In this system, when the fixed unit is connected to the plurality of scope units, and when the position of the connector portion is not aligned with that of the socket disposed opposite to the portion, the units cannot be connected to one another in some cases. When the position of the connector portion does not agree with that of the socket because of fluctuation by assembly during manufacturing, there is a problem that the scope unit cannot be attached/detached with respect to the fixed unit.

Furthermore, when the scope units cannot securely be positioned with respect to the fixed unit, loss of an illuminative light amount, or contact defect of an electric contact is caused, and original capabilities possessed by machines cannot be fulfilled in some case. Moreover, looseness or breakage is sometimes caused in a connected portion by vibration or impact. Therefore, since assembly accuracy has to be enhanced, a lot of trouble is taken, workability is bad, and further manufacturing cost is raised/influenced.

BRIEF SUMMARY OF THE INVENTION

According to the present invention, there is provided an endoscope apparatus comprising: a scope unit including an insertion portion to be inserted in an inspection object space, an observation unit for observation disposed in a tip end of the insertion portion, a curved portion which bends/operates the tip end of the insertion portion in an arbitrary direction, and a base unit connected to a base end of the insertion portion; and a fixed unit to which the base unit of the scope unit is detachably connected, wherein at least one of a connector on the side of the scope unit and a connector on the side of the fixed unit in a connector portion disposed in an detachable portion of the base unit and the fixed unit is a movable connector, and the detachable portion includes positioning means for positioning a connected position of the fixed unit side to the base unit side, when the connector on the side of the fixed connector is connected to that on the side of the base unit.

In the endoscope apparatus constituted in this manner, at least one of the connector on the side of the scope unit and that on the side of the fixed unit in the connector portion disposed in the detachable portion of the base unit of the scope unit and the fixed unit is the movable connector. The detachable portion is connected to the base unit and the fixed unit by the positioning sections for positioning the fixed unit side and the base unit side, when the connector on the side of the fixed unit is connected to that on the side of the base unit.

BRIEF DESCRIPTION OF THE SEVERAL VIEWS OF THE DRAWING

FIG. 16 is a schematic constitution diagram showing the inside of the fixed unit and the base unit in the scope unit in the endoscope apparatus of the first embodiment;

FIG. 19 is a longitudinal sectional view of a direct-sight binocular adapter for stereo measurement in the endoscope apparatus of the first embodiment;

FIG. 20 is a longitudinal sectional view of a side-sight binocular adapter in the endoscope apparatus of the first embodiment;

DETAILED DESCRIPTION OF THE INVENTION

Embodiments of the present invention will hereinafter be described in detail with reference to the drawings.

Figure 1:
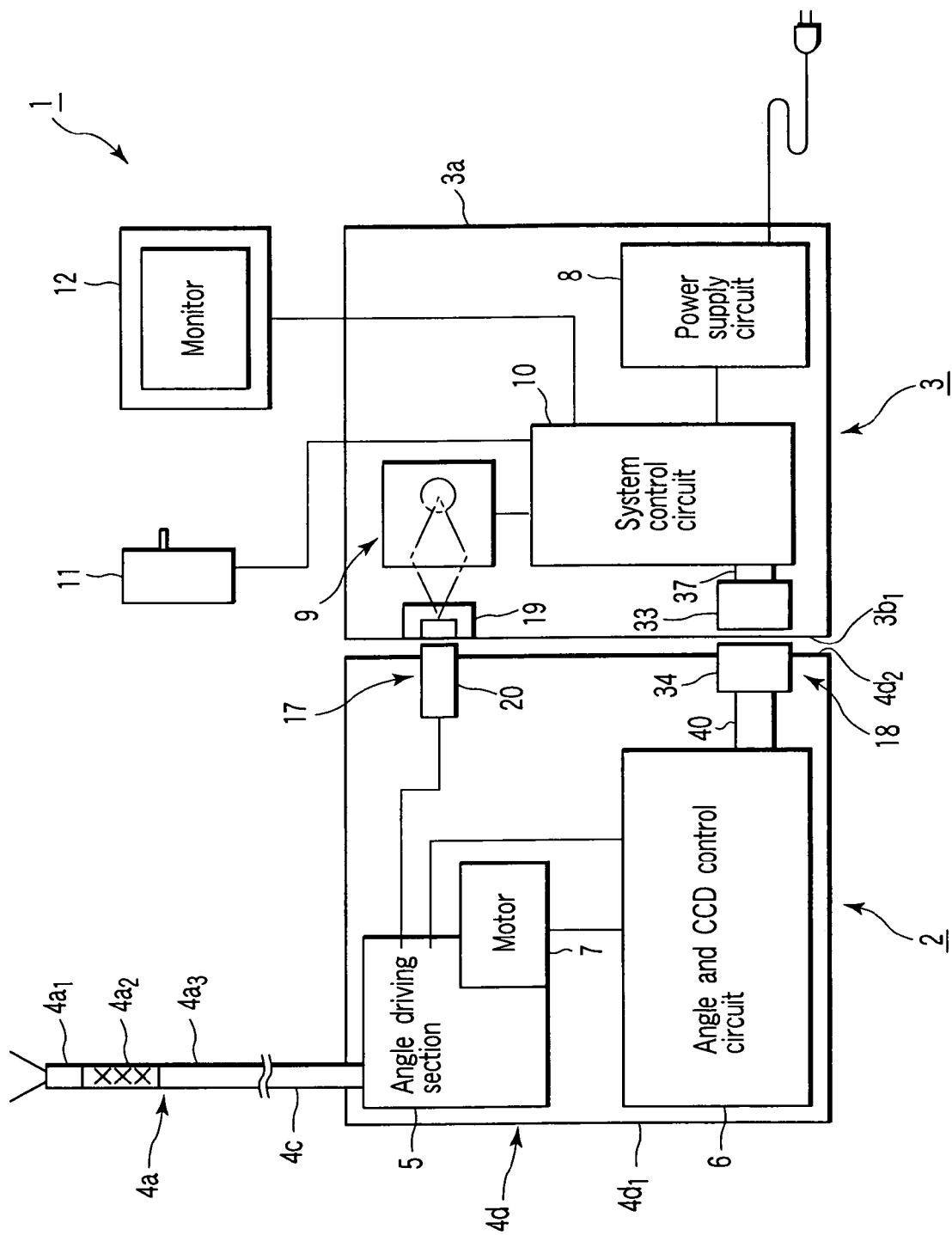
FIG. 1 is a schematic constitution diagram of a whole endoscope apparatus of a first embodiment of the present invention.

FIG. 1 shows a schematic constitution of a whole system of an endoscope apparatus 1 which is used in industry of an embodiment of the present invention. This system is constituted of: a scope unit 2 in which a plurality of different types of machines are disposed beforehand; and one fixed unit 3 usable in common with a plurality of types of scope units 2.

Figure 2:
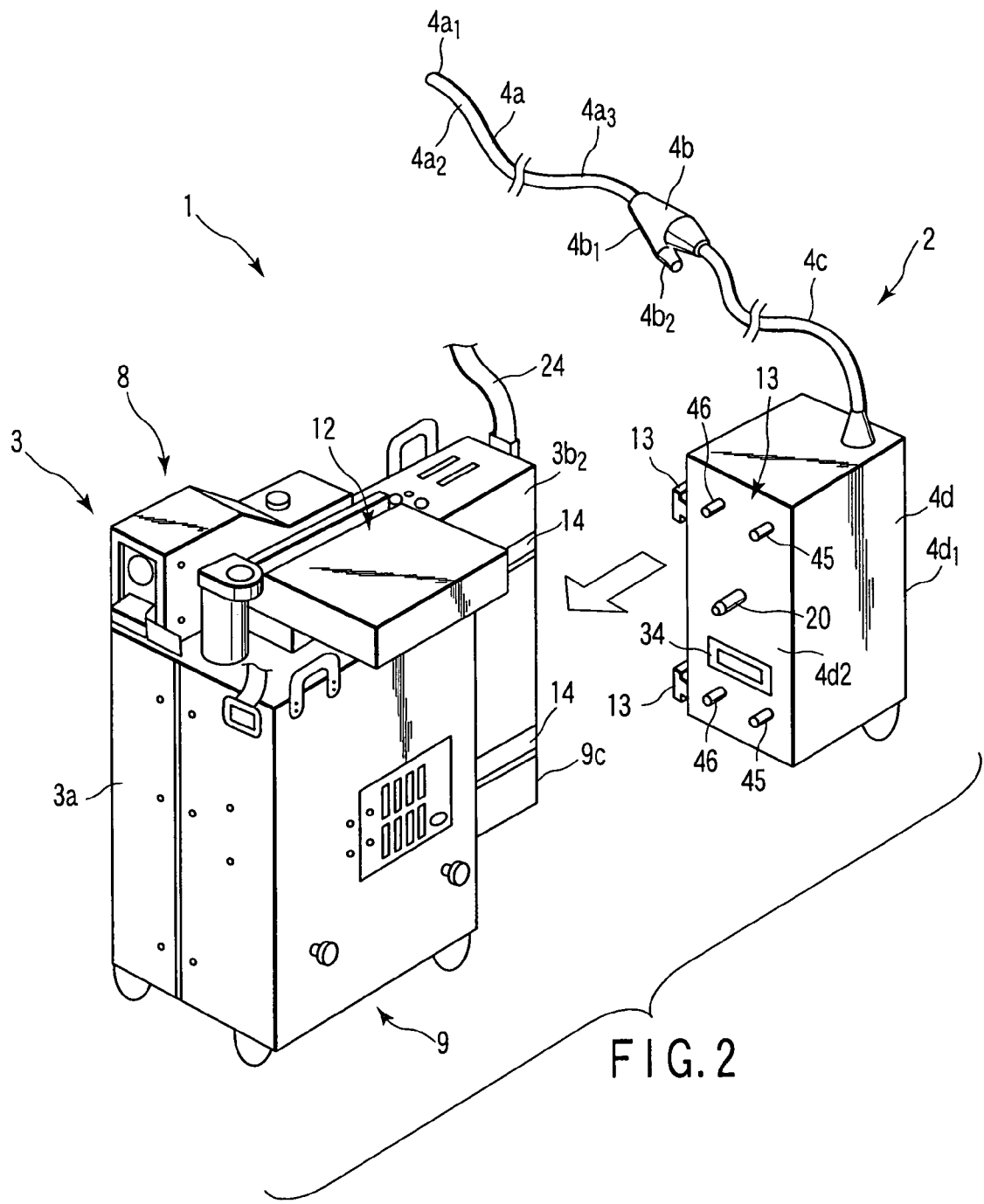
FIG. 2 is a perspective view showing that a base unit of a scope unit is detached from a fixed unit in the endoscope apparatus of the first embodiment.

Furthermore, as shown in FIG. 2, the scope unit 2 includes an elongated insertion portion 4a which is to be inserted into at least an inspection object space and which has flexibility; an intermediate connection portion 4b; a universal cable 4c;

and a base unit 4d. This insertion portion 4a does not have to necessarily have flexibility. Here, the insertion portion 4a is disposed in an endmost position, and is constituted of: a head portion 4a1 in which an observation optical system for observation, an illuminating optical system, and the like are incorporated; a curved portion 4a2 which can remotely be bent/operated; and an elongated flexible tube portion 4a3. Moreover, the curved portion 4a2 is disposed between the head portion 4a1 and the flexible tube portion 4a3.

Moreover, in a tip-end surface of the head portion 4a1, as shown in FIG. 16, an illuminating window 104 for the illuminating optical system, an observation window 106 for the observation optical system, a tip-end opening 101 of an inner channel (treatment instrument insertion path) 102 disposed inside the insertion portion 4a, and the like are disposed. Furthermore, inside the insertion portion 4a, a light guide for transmitting an illuminative light into the illuminating window, a signal line connected to solid image pickup devices such as a CCD disposed in the observation optical system, a plurality of, four in the present embodiment, angle wires (operation wires) for bending/operating the curved portion 4a2, and the like are arranged. In this example, two angle wires for vertical curve-operation, and two angle wires for left/right curve operation are arranged. Moreover, the curved portion 4a2 of the insertion portion 4a is pulled/operated in a vertical direction by two angle wires for the vertical curve operation and in a left/right direction by two angle wires for the left/right curve operation, and can be bent/deformed in four directions including the vertical and left/right directions, and an arbitrary direction obtained by combining these directions. It is to be noted that the operation is not limited to that by two angle wires.

Moreover, a base end of the flexible tube portion 4a3 of the insertion portion 4a is connected to the tip end of the intermediate connection portion 4b. The intermediate connection portion 4b includes a grip portion 4b1 which can be grasped with one hand by a user as shown in FIG. 2. In a rear end of the grip portion 4b1, a channel port portion 4b2 and a connection portion to the tip end of the universal cable 4c are juxtaposed. Furthermore, inside the universal cable 4c, a light guide extended from the insertion portion 4a side, the signal line, four angle wires, and the like are arranged.

Figure 4C:
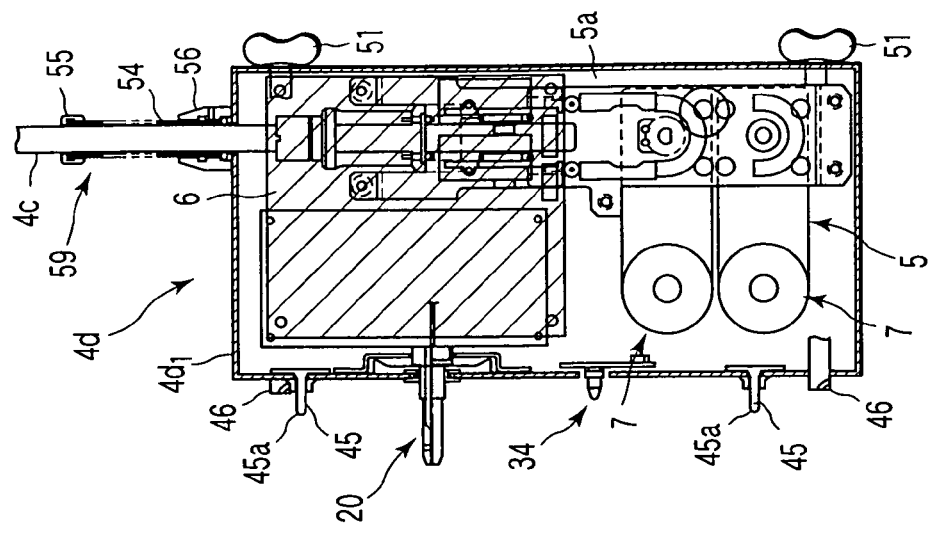
FIG. 4C is a sectional view along line IVC—IVC of FIG. 4B.
Figure 4B:
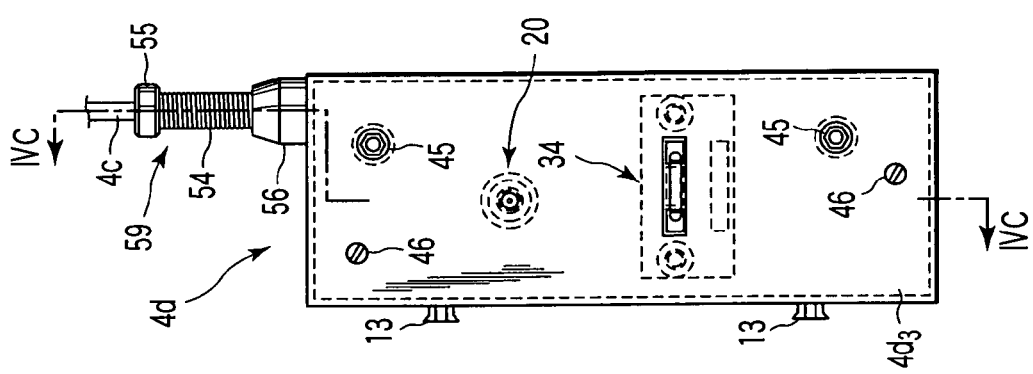
FIG. 4B is a front view of the unit.

Furthermore, the base end of the universal cable 4c is connected to the base unit 4d. For the base unit 4d, as shown in FIG. 1, inside a unit case 4d1, an angle driving section (curve control mechanism) 5, and an angle and CCD control circuit 6 are built. Here, in the angle driving section 5, as shown in FIG. 4C, a tractive force transmission mechanism unit 5a, and two motor units 7 for the vertical curve operation and left/right curve operation, respectively, are constituted. Furthermore, in the angle and CCD control circuit 6, a control circuit of an image pickup device constituting a camera control unit (CCU), a curve control circuit for controlling the operation of the angle driving section 5, a circuit relay substrate, and the like are built.

For the fixed unit 3, a unit case 3a contains a power supply unit 8, light source unit (lamp) 9, system control circuit 10, lamp lighting circuit, circuit relay substrate, and the like. Furthermore, the system control circuit 10 can be connected to an operation remote controller 11 for operating the endoscope apparatus 1, and a monitor 12 which performs display.

Figure 3:
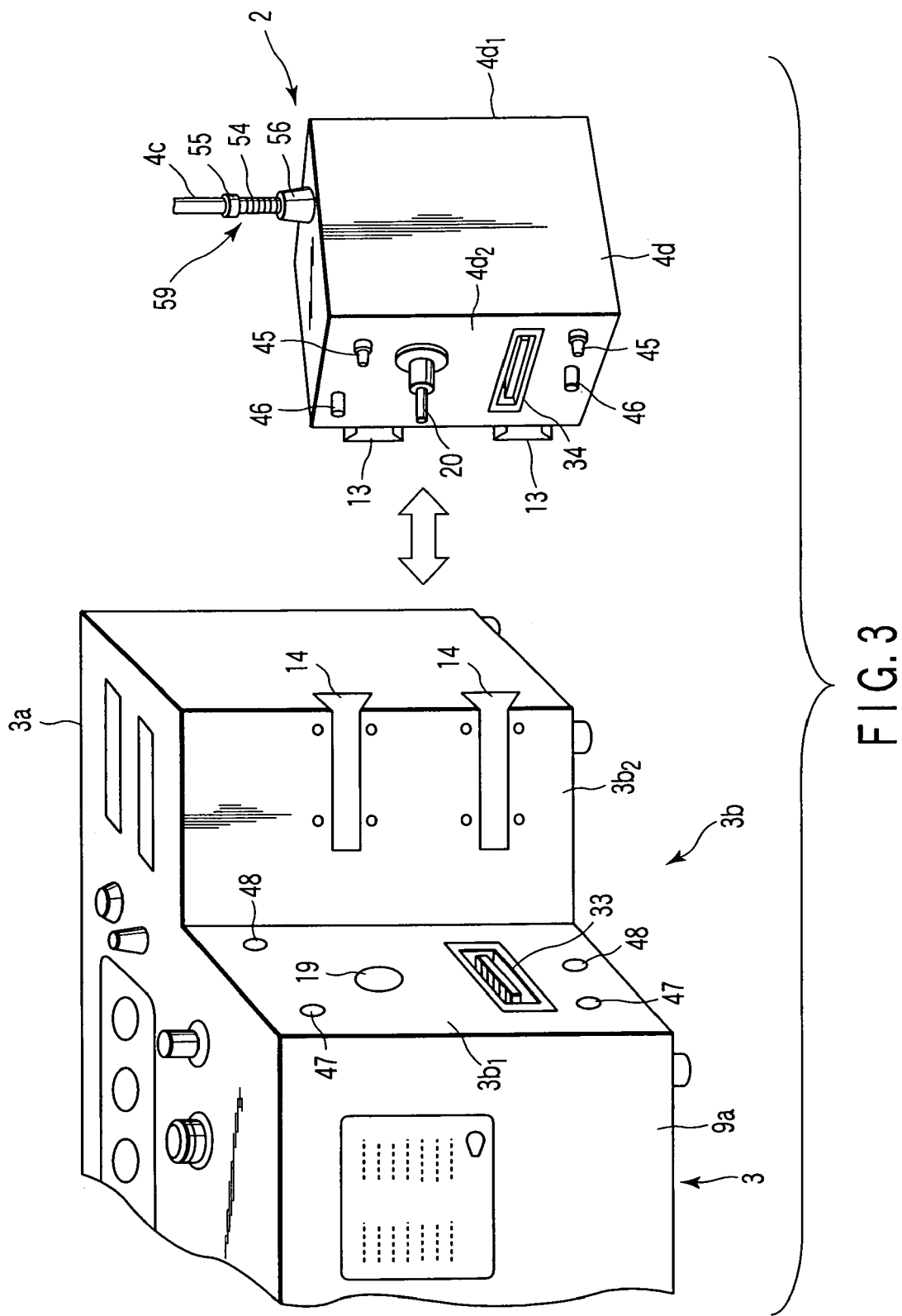
FIG. 3 is a perspective view showing an detachable portion of the base unit of the scope unit and the fixed unit in the endoscope apparatus of the first embodiment.

Moreover, as shown in FIG. 3, in the unit case 3a of the fixed unit 3, a scope unit connection portion 3b is formed to which the base unit 4d of the scope unit 2 is detachably connected and which has a concave shape. In the scope unit connection portion 3b, a scope unit connection surface 3b1 which abuts on an end plate (housing panel) 4d2 of the unit case 4d1 in the base unit 4d of the scope unit 2, and a scope unit contact surface 3b2 which contacts a side plate 4d3 of the unit case 4d1 are arranged.

The scope unit connection surface 3b1 is formed by a lamp housing 9a of the light source unit 9 in the fixed unit 3.

Figure 4A:
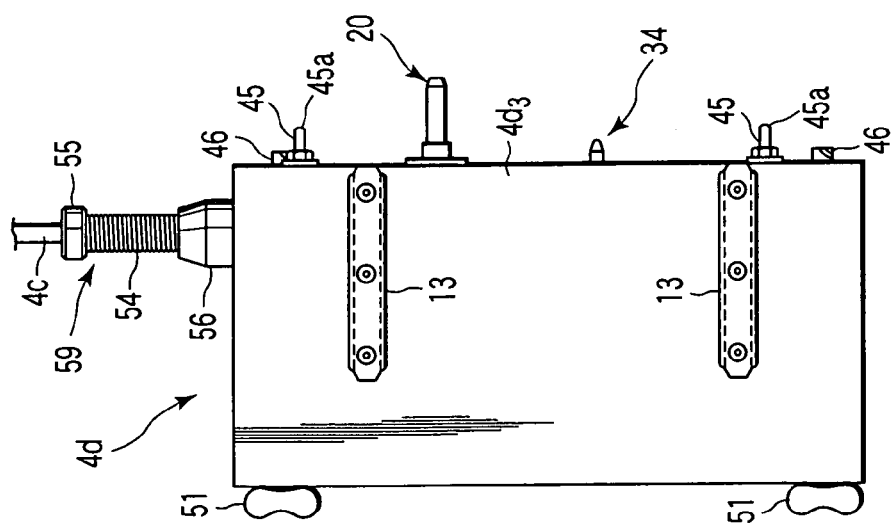
FIG. 4A is a side view of the base unit of the scope unit in the endoscope apparatus of the first embodiment.
Figure 5:
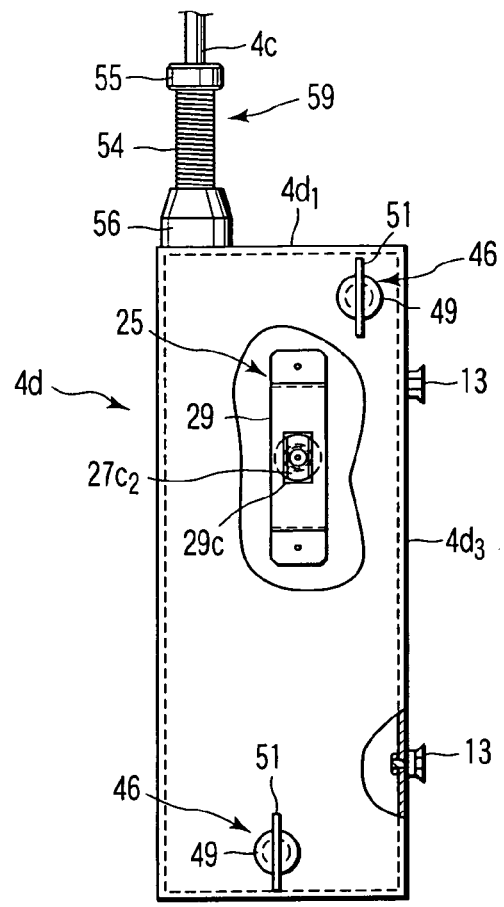
FIG. 5 is a rear view of the base unit of the scope unit in the endoscope apparatus of the first embodiment.

Moreover, as shown in FIGS. 4A, B, and 5, in the side plate 4d3 of the unit case 4d1 of the base unit 4d, two upper and lower protrusion-shaped resin slider members 13 which guide movement of the base unit 4d at the time of connection with respect to the fixed unit 3 are extended substantially along a horizontal direction. Here, in the fixed unit 3, guide rails 14 formed of a metal are disposed to guide the movement of the slider members 13. As shown in FIG. 6, in an inner surface of the guide rail 14, a dovetail groove 14a is formed which has tapered surfaces 14a1 engaging with the slider member 13.

Figure 6A:
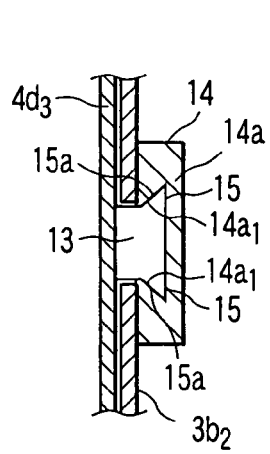
FIG. 6A is a longitudinal sectional view showing a fitted portion of a guide rail on the side of the fixed unit of the endoscope apparatus of the first embodiment into a slider on the side of the base unit of the scope unit.

Moreover, as shown in FIG. 4A, the slider members 13 are screwed/fixed to the side plate 4d3 of the unit case 4d1. Furthermore, as shown in FIG. 6A, vertically extended projecting portions 15 are disposed on opposite upper/lower ends of each slider member 13. On the inner surfaces of the respective projecting portions 15, engaging surfaces 15a having tapered surface shape are formed to fit into the dovetail groove 14a of the slider member 13.

Figure 6B:
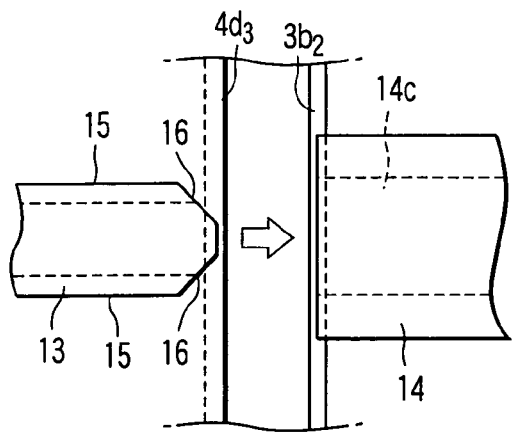
FIG. 6B is a side view showing a state before the guide rail on the side of the fixed unit is fitted into the slider on the side of the base unit of the scope unit.

Furthermore, in opposite front/rear ends of each slider member 13, as shown in FIG. 6B, chamfered portions 16 obtained by largely cutting the end surface portion are formed so that the member is easily inserted into the dovetail groove 14a constituting the guide rail 14. Additionally, the slider member 13 of the base unit 4d is inserted into the dovetail groove 14a of the guide rail 14 of the fixed unit 3, when the fixed unit 3 is connected to the base unit 4d of the scope unit 2. Furthermore, the slider member 13 slides along the dovetail groove 14a of the guide rail 14 to guide the movement of the base unit 4d. It is to be noted that when a gap between the dovetail groove 14a and the slider member 13 is large, connectors cannot be positioned as described later, and therefore the groove and member need to be formed to be fitted into each other as closely as possible. However, when the member is too closely fitted, it becomes difficult to insert the member, and therefore the chamfered portions 16 are formed on the opposite front/rear ends of each slider member 13.

Moreover, as shown in FIG. 1, in the scope unit connection surface 3b1 and the end plate (housing panel) 4d2 of the base unit 4d, an optical connector portion 17 for optical connection and a connector portion 18 for electric connection are detachably disposed.

Furthermore, the optical connector portion 17 includes: a light source side optical connector 19 which is a fixed connector relatively firmly attached to the fixed unit 3 with good positional accuracy; and a light guide connector (hereinafter referred to as an LG connector) 20 which is a movable connector attached to the base unit 4d in a slightly movable state with a backlash (play).

Figure 7A:
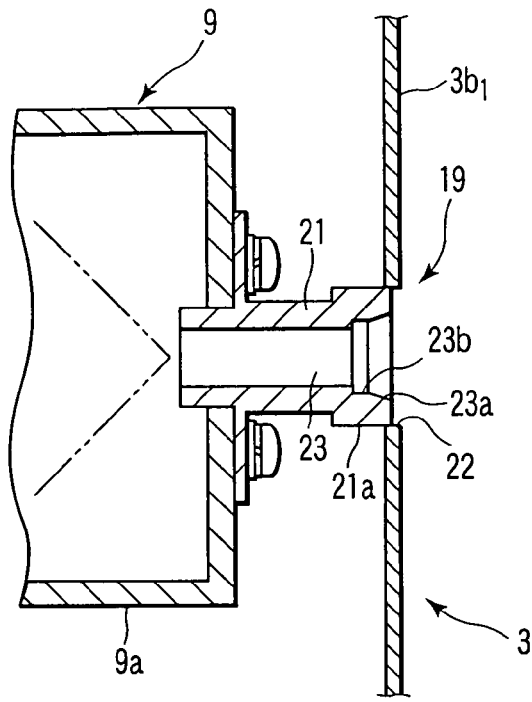
FIG. 7A is a longitudinal sectional view showing an attached state of a connector block in the fixed unit of the first embodiment.

FIG. 7A shows an attached state of the light source side optical connector 19.

The light source side optical connector 19 is constituted of a schematically tubular connector block (receiving member) 21 which fits into the LG connector 20, and the base end of the connector is screwed/constituted in the lamp housing 9a of the light source unit 9.

Furthermore, in the tip end of the connector block 21, a metal cap portion 21a is disposed which broadens in a tapered state. The metal cap portion 21a is attached to a connector mounting hole 22 formed in the scope unit connection surface 3b1 of the fixed unit 3.

Moreover, an LG connector insertion hole 23 into which the LG connector 20 is inserted is formed in the tube of the connector block 21. In the tip end of the LG connector insertion hole 23, a metal cap tapered portion (tapered fitting hole portion) 23a whose inner diameter gradually increases toward the outside is formed so that the LG connector 20 is easily inserted into a mouth of the connector block 21. The metal cap tapered portion 23a includes a step portion 23b which constitutes an abutment surface at the time of insertion of the LG connector 20 into a rear end position.

Figure 7B:
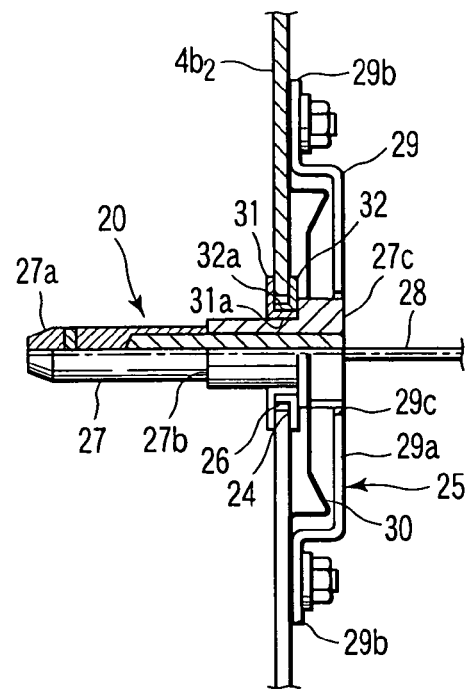
FIG. 7B is a longitudinal sectional view showing the attached state of a light guide connector on the side of the base unit of the scope unit.

Moreover, FIG. 7B shows the attached state of the LG connector 20.

An LG connector attachment hole 24 is formed in the end plate 4d2 of the unit case 4d1. The LG connector 20 is inserted into the attachment hole 24, and attached by an LG connector support portion 25. The LG connector support portion 25 includes a play portion 26 which permits the backlash between both the connectors during attachment/detachment of the LG connector 20 with respect to the light source side optical connector 19 of the fixed unit 3.

Moreover, an LG connector main body 27 having a substantially shaft shape is disposed in the LG connector 20. A shaft center portion of the LG connector main body 27 is connected to the base end of a light guide 28 extended from the universal cable 4c side.

Furthermore, in the tip end of the LG connector main body 27, a tapered portion 27a is disposed so that the main body is easily inserted into the connector block 21 on the fixed unit 3 side. A step portion 27b which is to be disposed opposite to the abutment surface of the step portion 23b of the connector block 21 is disposed halfway in the LG connector main body 27.

Figure 8:
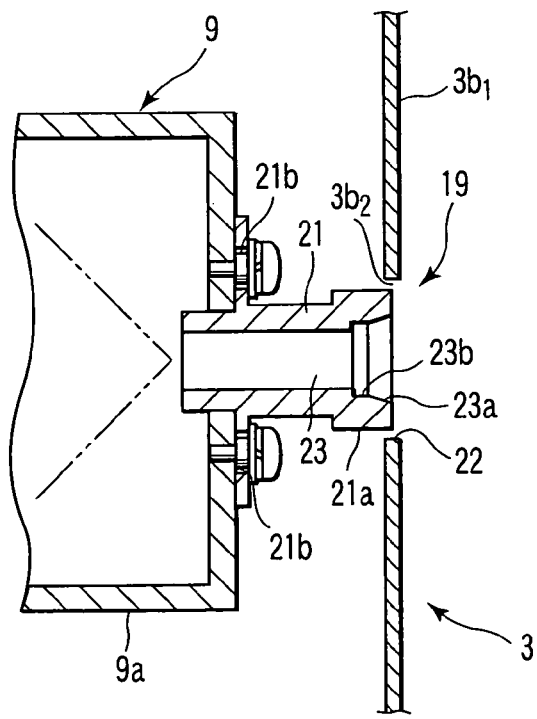
FIG. 8 is a longitudinal sectional view showing the attached state of the connector block including a play portion in the fixed unit of the first embodiment.

FIG. 8 shows a modification example of the light source side optical connector 19 shown in FIG. 7A described above. The play portion 26 which permits the backlash at the time of connection is disposed in the LG connector 20 of FIG. 7B, but a play portion 21b which permits the backlash is similarly disposed also in the light source side optical connector 19. When the play portion 21b is disposed, a gap 3b2 is disposed to increase the diameter of the connector mounting hole 22 so that a backlash width in the play portion 21b can be handled.

By this constitution, since both the play portion 26 on the LG connector 20 side of FIG. 7B and the play portion 21b on the light source side optical connector 19 side, a deviation width permitted at the time of attachment increases, and the positioning by an operator in an attachment operation is facilitated.

Figure 9A:
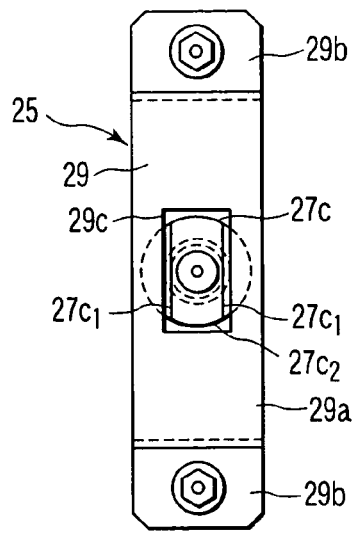
FIG. 9A is a plan view showing an attached portion of the light guide connector on the side of the base unit of the scope unit of the first embodiment.
Figure 9B:
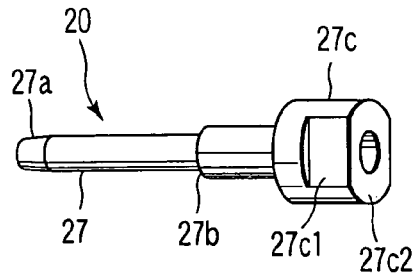
FIG. 9B is a perspective view showing the light guide connector.

Moreover, as shown in FIG. 9B, a large-diameter shaft portion 27c is formed in a root side end of the LG connector main body 27. A D cut portion 27c1 obtained by cutting opposite side surfaces is formed in the rear end of the large-diameter shaft portion 27c.

Furthermore, as shown in FIG. 7B, the LG connector support portion 25 includes a connector receiving member 29, leaf spring member 30, two connector receiving rings, that is, first connector receiving ring 31 and second connector receiving ring 32. Here, a small-diameter cylindrical portion 31a is disposed on the inner peripheral edge of the first connector receiving ring 31. The inner peripheral surface of the small-diameter cylindrical portion 31a of the first connector receiving ring 31 is fitted into the outer peripheral surface of the LG connector 20.

Additionally, a male screw portion is formed in the outer peripheral surface of the small-diameter cylindrical portion 31a of the first connector receiving ring 31. Furthermore, a meshing cylindrical portion 32a including a screw hole portion meshed with the small-diameter cylindrical portion 31a is formed in the inner peripheral edge of the second connector receiving ring 32. An outer diameter of the meshing cylindrical portion 32a is set to be smaller than an inner diameter of the LG connector attachment hole 24.

Moreover, the first connector receiving ring 31 and second connector receiving ring 32 are fitted into the opposite surfaces of the end plate 4d2 of the unit case 4d1. These first connector receiving ring 31 and second connector receiving ring 32 mesh with each other by screws disposed on both the components, and are integrated. At this time, the play portion 26 is formed of a space between the meshing cylindrical portion 32a of the second connector receiving ring 32 and the LG connector attachment hole 24. Moreover, the integrated first and second connector receiving rings 31, 32 are attached to the end plate 4d2 of the unit case 4d1, and in this state the rings can freely move in a range of the play portion 26 in a direction crossing at right angles to an axial direction of the LG connector 20. Accordingly, the LG connector 20 can freely move in the range of the play portion 26 in the direction crossing at right angles to the axial direction of the LG connector 20.

Moreover, in the connector receiving member 29, substantially L-shaped leg portions 29b are bent/formed in the opposite ends of a base plate 29a having a substantially flat plate shape. Furthermore, a square hole 29c having a rectangular shape is formed substantially in a middle position of the base plate 29a.

Furthermore, the leaf spring member 30 is disposed inside the connector receiving member 29. This leaf spring member 30 includes a square hole through which a shaft portion 27c2 between both the D cut portions 27c1 in the root side end of the LG connector 20 is inserted. Furthermore, the shaft portion 27c2 between both the D cut portions 27c1 of the root side end of the LG connector 20 is inserted through the square hole 29c of the connector receiving member 29.

As shown in FIG. 9A, a dimension of the square hole 29c is set to be slightly larger than the section of the shaft portion 27c2 between both the D cut portions 27c1 in the root side end of the LG connector 20. It is to be noted that the square hole 29c does not limit the movement in the direction crossing at right angles to the axial direction of the LG connector 20 by the backlash of the LG connector 20, that is, in a range of the play portion 26. Furthermore, by a fitted portion of the shaft portion 27c2 between the D cut portions 27c1 on the opposite sides of the large-diameter shaft portion 27c of the LG connector main body 27 into the square hole 29c, a rotary angle of the LG connector 20 is regulated. Therefore, the light guide 28 is prevented from being twisted or broken.

Moreover, as shown in FIG. 7B, the leg portions 29b of the connector receiving member 29 are both fastened with respect to the end plate 4d2 of the unit case 4d1 together with the leaf spring member 30 by fixing screws. At this time, when strength of the connector receiving member 29 is sufficiently increased, and when the LG connector 20 abuts on another component, a limitation is made such that the LG connector 20 can move in an elastic region of the leaf spring member 30. This prevents the LG connector 20 from compressing or breaking the inner components.

Furthermore, at the time of the connection of the light source side optical connector 19 of the optical connector portion 17 to the LG connector 20, the LG connector 20 of the scope unit 2 is inserted into the tube of the connector block 21 of the fixed unit 3. At this time, the connector block 21 is attached to the connector mounting hole 22 of the fixed unit 3 with good positional accuracy, and relatively firmly fixed. On the other hand, the LG connector 20 is supported by the LG connector support portion 25 with the backlash (play) in such a manner that the connector can slightly move with respect to the end plate 4*d*2 of the unit case 4*d*1 of the scope unit 2. Therefore, the backlash between both the connectors at the time of attachment/detachment of the LG connector 20 with respect to the light source side optical connector 19 of the fixed unit 3 can be absorbed by free movement within the range of the play portion 26 of the LG connector support portion 25 in the direction crossing at right angles to the axial direction of the LG connector 20. It is to be noted that when the play portions 26, 21*b* are disposed both in the light source side optical connector 19 and LG connector 20 as shown in FIG. 8, the backlash of these added ranges can be obtained at maximum. Moreover, the tapered portion 27*a* of the tip end of the LG connector 20 abuts on the metal cap tapered portion 23*a* of the connector block 21, and is guided along the metal cap tapered portion 23*a*, and in this state the LG connector 20 is inserted into the LG connector insertion hole 23. This forms axial alignment means for carrying out axial alignment between the light source side optical connector 19 and LG connector 20 of the fixed unit 3 at the time of the connection.

Moreover, when the LG connector 20 is fitted into the connector block 21, the connector block 21 is positioned in accordance with a lamp (not shown) so that an optical axis of the lamp (not shown) in the light source unit 9 is coaxial with the end surface of the light guide 28 of the LG connector 20. Accordingly, an illuminative light of the lamp (not shown) in the light source unit 9 is converged onto the end surface of the LG connector 20.

Furthermore, as shown in FIG. 1, in the connector portion 18 between the scope unit connection surface 3*b*1 of the fixed unit 3 and the end plate 4*d*2 of the base unit 4*d* of the scope unit 2, a fixed unit side connector (fixed connector) 33 attached to the fixed unit 3 in a standard position, and a scope side connector (movable connector) 34 attached to the base unit 4*d* are disposed.

Figure 11A:
FIG. 11A is a plan view showing the connector on the side of the fixed unit in the scope unit of the first embodiment.
Figure 11B:
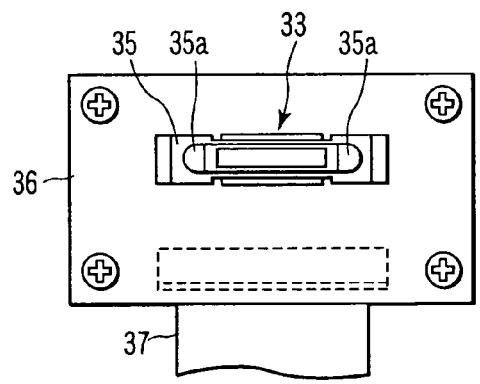
FIG. 11B is a plan view showing that the connector is attached to the attachment substrate of the connector.

FIGS. 11A, 11B show the fixed unit side connector 33 (hereinafter referred to as the connector 33). A connector main body 35 of this connector 33 is mounted on a substrate 36. This substrate 36 is connected to one end of a harness 37. The other end of the harness 37 is connected to the system control circuit 10 in the fixed unit 3.

Figure 11C:
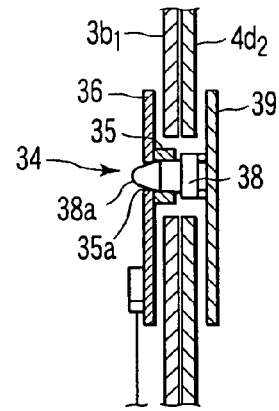
FIG. 11C is a longitudinal -sectional view of a major part showing a connected state of the connector of the base unit in the scope unit with respect to the connector on the side of the fixed unit.

Moreover, as shown in FIG. 11B, connector concave portions 35*a* for the positioning are disposed in the opposite ends of the connector main body 35. Furthermore, as shown in FIG. 11C, the substrate 36 on which the connector 33 is mounted is fixed to the end plate 4*d*2 of the unit case 4*d*1 with high positional accuracy.

Furthermore, FIGS. 10A to 11C show the scope side connector 34 (hereinafter referred to as the connector 34). A connector main body 38 of the connector 34 is mounted on a substrate 39. This substrate 39 is connected to one end of a harness 40. The other end of the harness 40 is connected to the angle and CCD control circuit 6 in the scope unit 2.

Figure 10A:
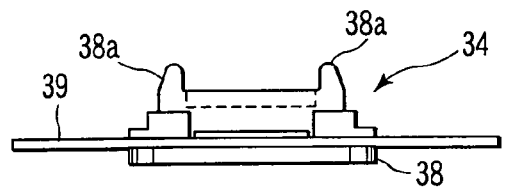
FIG. 10A is a plan view showing the connector of the base unit in the scope unit of the first embodiment.

Additionally, as shown in FIG. 10A, connector convex portions 38*a* for the positioning are disposed on the opposite ends of the connector main body 38. These connector convex portions 38*a* are disposed in positions disposed opposite to two connector concave portions 35*a* of the connector 33.

Figure 10C:
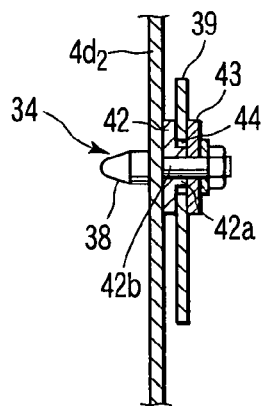
FIG. 10C is a sectional view along line IXC—IXC of FIG. 10B.
Figure 10B:
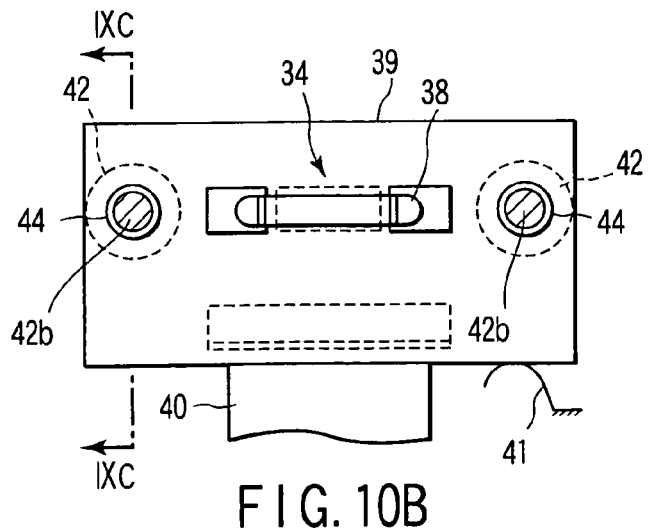
FIG. 10B is a plan view showing that the connector is attached to an attachment substrate of the connector.

Moreover, as shown in FIG. 10C, the substrate 39 on which the connector 34 is mounted is fixed to the end plate 4*d*2 of the unit case 4*d*1 via two substantially annular spacer rings, that is, a first spacer ring 42 and second spacer ring 43. Here, a small-diameter cylindrical portion 42*a* is disposed on the inner peripheral edge of the first spacer ring 42. The inner peripheral surface of the small-diameter cylindrical portion 42*a* of the first spacer ring 42 is fitted with the outer peripheral surface of a support shaft 42*b* of the substrate 39. The outer diameter of the support shaft 42*b* is set to be smaller than the inner diameter of a substrate attachment hole 44 formed in the substrate 39. Moreover, the substrate 39 can freely move in the range of the gap between the support shaft 42*b* of the substrate 39 and the substrate attachment hole 44 in the direction crossing at right angles to the fixed to of the support shaft 42*b*. This forms the play portion which permits the backlash between both the connectors at the time of the attachment/detachment of the connector 33 with respect to the connector 34. It is to be noted that the substrate 39 may also be urged by a spring member 41 so as to prevent the substrate 39 from rattling because of vibration as shown in FIG. 10B.

Furthermore, when the connector convex portions 38*a* on the opposite ends of the connector main body 38 are fitted into two connector concave portions 35*a* of the connector 33 at the time of the connection of the connector 33 of the connector portion 18 with respect to the connector 34, the axial alignment is carried out to determine the positions of the connector convex portions 38*a* of the opposite ends of the connector main body 38 in accordance with those of the connector concave portions 35*a*.

Additionally, when the substrate 39 of the connector 34 moves in the range of the gap between the support shaft 42*b* of the substrate 39 and the substrate attachment hole 44 at the time of the connection of the connector 33 with respect to the connector 34, the connector convex portions 38*a* of the connector main body 38 are inserted and smoothly coupled into the connector concave portions 35*a* of the connector main body 35.

Moreover, as shown in FIG. 3, a guide pin 45 and lock member 46 are disposed on the upper end of the end plate 4*d*2 of the base unit 4*d* of the scope unit 2. Furthermore, the guide pin 45 and lock member 46 are similarly disposed on the lower end of the end plate 4*d*2 of the base unit 4*d*.

Figure 15:
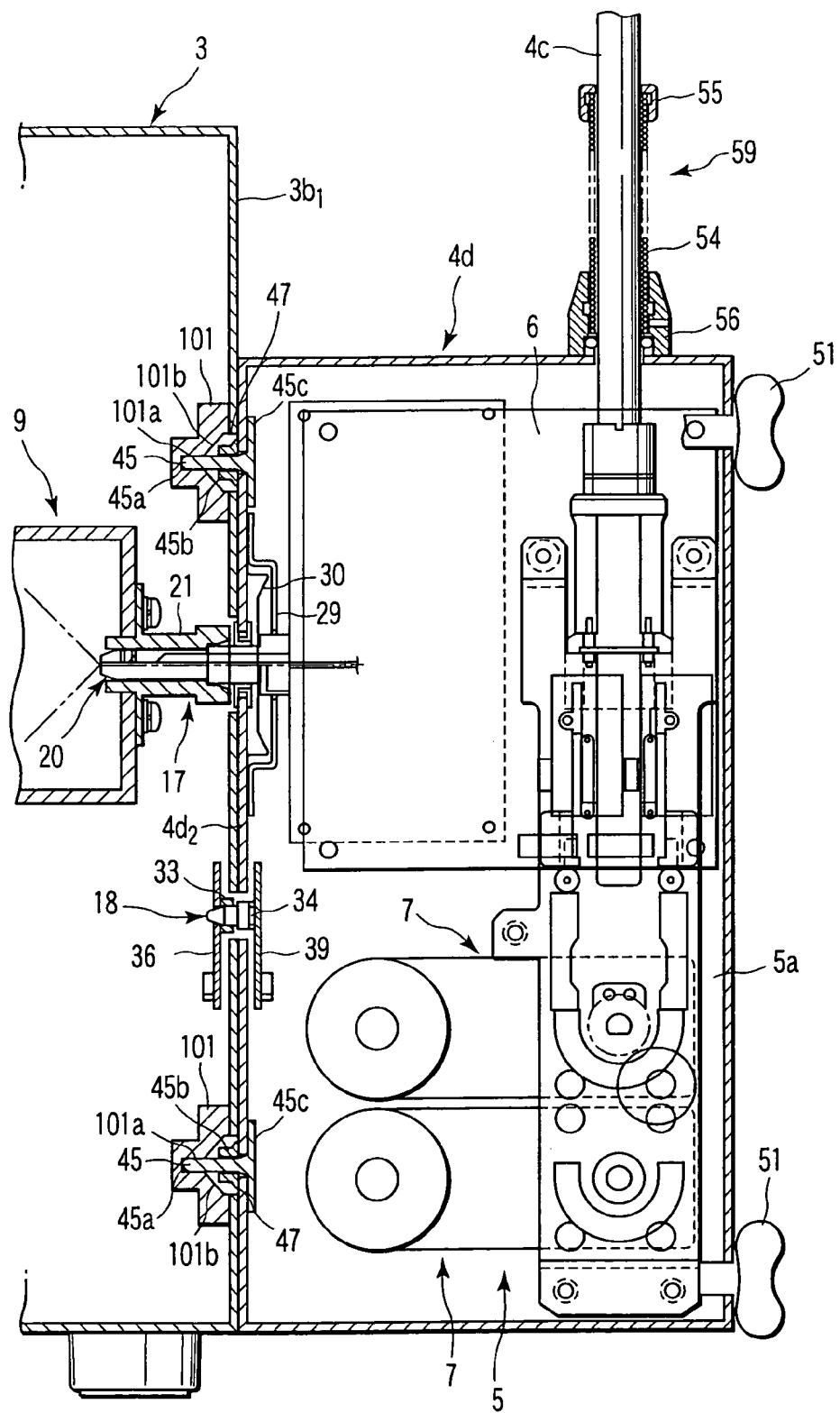
FIG. 15 is a longitudinal sectional view showing a connected state of the fixed unit with respect to the base unit in the scope unit of the endoscope apparatus of the first embodiment.

As shown in FIG. 15, a flange portion 45*c* is formed on the base end of the shaft member of the guide pin 45. This guide pin 45 passes through the back surface of the end plate 4*d*2 of the unit case 4*d*1, and is fixed by a nut 45*b*. Accordingly, high positional accuracy is obtained with simple assembling. At this time, the guide pin 45 is attached to the end plate 4*d*2 of the unit case 41 with the high positional accuracy. Furthermore, a tapered portion 45*a* is formed in the tip end of the shaft member of the guide pin 45 to facilitate the fitting.

Moreover, as shown in FIG. 15, a guide pin receiving member 47 is attached with the high positional accuracy to the scope unit connection surface 3*b*1 of the fixed unit 3 in a position disposed opposite to the guide pin 45 of the base unit 4*d*. A pin insertion hole 101*a* into which the guide pin 45 is to be inserted is formed in a main body 101 of the guide pin receiving member 47. A tapered surface 101*b* is formed on the mouth of the pin insertion hole 101*a* so as to facilitate the fitting.

Figure 12A:
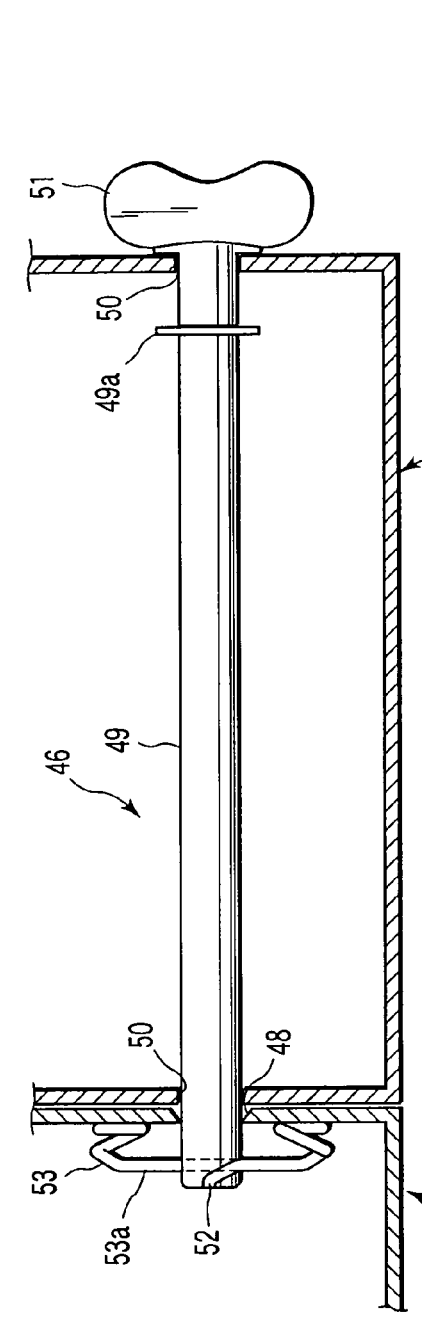
FIG. 12A is a longitudinal sectional view of a major part showing the attached state of a fixing member of the fixed unit with respect to the base unit in the scope unit of the endoscope apparatus of the first embodiment.

Furthermore, FIG. 12A shows the lock member 46 which is connection holding means for fastening/fixing the fixed unit 3 and the base unit 4*d* of the scope unit 2 at the time of the connection of housings. This lock member 46 includes a shaft 49 extended through the base unit 4*d* on the opposite sides of shaft insertion holes 50. A knob 51 disposed outside the base unit 4*d* is disposed in the base end of the shaft 49.

Furthermore, a substantially spiral lock groove 52 is formed in the tip end of the shaft 49. It is to be noted that an E ring attachment groove is formed in the middle of the shaft 49, and an E ring 49*a* disposed in the E ring attachment groove prevents the scope unit 2 from coming off the shaft 49.

Additionally, a lock hole 48 is formed in a position opposite to the lock member 46 of the scope unit 2 in a housing panel in the scope unit connection surface 3*b*1 of the fixed unit 3. A spring member 53 for locking the lock member 46 is fixed to the back surface of the scope unit connection surface 3*b*1 around the lock hole 48. A linear engaging portion 53*a* is formed in the spring member 53. The engaging portion 53*a* engages with the lock groove 52 in the tip end of the shaft 49 of the lock member 46 so as to be engageable/disengageable.

Next, a function of the above-described constitution will be described. At the time of the use of the endoscope apparatus 1 of the present embodiment, the base unit 4*d* of the scope unit 2 is detachably connected to the scope unit connection portion 3*b* of the unit case 3*a* of the fixed unit 3. At the time of the connection operation of the base unit 4*d*, the slider members 13 of the scope unit 2 are inserted into the guide rails 14 of the fixed unit 3. In this state, when the scope unit 2 is slid along the guide rails 14 on the fixed unit 3 side, first the LG connector 20 abuts on the connector block 21 of the fixed unit 3.

At this time, the LG connector 20 slightly moves in the direction (X-Y direction) crossing at right angles to the axial direction. When the scope unit 2 is pushed in, the LG connector 20 enters the connector block 21.

The tip-end surface of the LG connector 20 reaches a predetermined position in which the light of the lamp of the light source unit 9 in the fixed unit 3 is converged. Then, the step portion 23*b* disposed as the abutment surface halfway in the connector block 21 abuts on the step portion 27*b* disposed as the abutment surface halfway in the LG connector 20.

When the LG connector 20 is further pushed in from this position, the LG connector 20 urged by the leaf spring member 30 is unchanged, and the leaf spring member 30 is elastically deformed into a sunk state. Therefore, when one fixed unit 3 is selectively combined with a plurality of types of scope units 2, the position of the end surface of the LG connector 20 is constantly maintained in the same position even with scatterings among the plurality of individual types of scope units 2.

Furthermore, during the connection operation of the LG connector 20 with respect to the connector block 21, the main body 101 of the guide pin receiving member 47 abuts on the shaft member of the guide pin 45 on the scope unit 2 side with an operation of pushing the base unit 4*d* of the scope unit 2 toward the fixed unit 3. At this time, when the tapered surface 101*b* of the guide pin receiving member 47 abuts on the tapered portion 45*a* of the guide pin 45, the tip end of the guide pin 45 is smoothly inserted and fitted into the pin insertion hole 101*a*. This determines a positional relation between the fixed unit 3 and the base unit 4*d* of the scope unit 2 in the axial direction (Z direction) and the direction (X-Y direction) crossing at right angles to the axial direction.

Subsequently, the connector 33 of the connector portion 18 is connected to the connector 34. At the time of the connection of the connector portion 18, first the connector concave portions 35*a* of the connector 33 are allowed to abut on the connector convex portions 38*a* of the connector 34.

At this time, the connector 34 slightly moves in the direction (X-Y direction) crossing at right angles to the axial direction by the concave/convex portion, and the connector convex portions 38*a* of the connector main body 38 are inserted into two connector concave portions 35*a* of the connector 33. In this state, when the scope unit 2 is further pushed in, the connector 33 fits with the connector 34, and mutual contact points contact with each other so as to be conductive. The connector 33 integrally connected to the connector 34 does not move even when vibration is applied, and secure conduction is secured.

Thereafter, the lock member 46 is used. At the time of the use of the lock member 46, the base unit 4*d* of the scope unit 2 is allowed to abut on the scope unit connection surface 3*b*1 of the fixed unit 3, and the shaft 49 is pushed while manually rotating the knob 51. At this time, the engaging portion 53*a* of the spring member 53 on the back surface of the housing panel of the scope unit connection surface 3*b*1 is fitted into the lock groove 52 in the tip end of the shaft 49.

When the shaft 49 is further rotated in this state, the engaging portion 53*a* of the spring member 53 is pulled in by the lock groove 52 of the shaft 49, and securely locked by a last portion of the lock groove 52. At this time, since the shaft 49 is constantly urged by a spring force of the spring member 53, the shaft is rotated in reverse, and the lock member 46 is not disengaged until the lock is released.

Therefore, the above-described constitution produces the following effect. That is, in the endoscope apparatus 1 of the present embodiment, the optical connector portion 17 includes the light source side optical connector 19 which is the fixed connector relatively firmly attached to the fixed unit 3 with the good positional accuracy, and the LG connector 20 which is the movable connector attached in the state with the backlash (play) such that the connector can slightly move with respect to the base unit 4*d*. Therefore, at the time of the connection of the light source side optical connector 19 which is the fixed connector with respect to the LG connector 20 which is the movable connector, the backlash between both the connectors at the time of the attachment/detachment of the LG connector 20 with respect to the light source side optical connector 19 can be permitted by the play portion 26 of the LG connector 20.

Furthermore, the tapered portion 27*a* of the tip end of the LG connector 20 abuts on the metal cap tapered portion 23*a* of the connector block 21, and is guided along the metal cap tapered portion 23*a*. When the LG connector 20 is inserted into the LG connector insertion hole 23 in this state, it is possible to carry out the axial direction between the light source side optical connector 19 which is the fixed connector and the LG connector 20 which is the movable connector.

Therefore, even when the position of the connector slightly fluctuates by the fluctuation of the assembling of the plurality of types of scope units 2, the light source side optical connector 19 can be connected to the LG connector 20 which is the movable connector without any problem. As a result, the plurality of types of scope units 2 can be changed so as to be detachable with respect to the fixed unit 3.

Furthermore, any loss of an illuminative light amount is not caused in the connected portion of the light source side optical connector 19 to the LG connector 20 which is the movable connector, and original capabilities of a machine can be fulfilled. Similarly, any contact defect of the electric contact is not caused even in the connector portion 18 for the electric connection, and the original capabilities of the machine can be fulfilled. Even when the vibration or impact is applied to the connected portion of the light source side optical connector 19 to the LG connector 20 which is the movable connector, the capabilities can be maintained.

It is to be noted that in the present embodiment the constitution including the light source side optical connector 19 disposed as the fixed connector in the fixed unit 3, and the LG connector 20 disposed as the movable connector in the base unit 4d of the scope unit 2 has been described. However, the light source side optical connector 19 of the fixed unit 3 may be replaced with the movable connector, and the LG connector 20 of the base unit 4d of the scope unit 2 may also be replaced with the fixed connector.

Moreover, in the present embodiment, when the base unit 4d of the scope unit 2 is attached to the fixed unit 3, the slider member 13 on the scope unit 2 side is aligned with the dovetail groove 14a of the guide rail 14 on the fixed unit 3 side, and is transversely slid, so that the connector can easily be connected.

Furthermore, even when the base unit 4d of the scope unit 2 is detached from the fixed unit 3, a sliding direction is determined. Therefore, there is no possibility that an impossible force is applied to break the optical connector portion 17 and connector portion 18 between the base unit 4d of the scope unit 2 and the fixed unit 3. Therefore, it is easy to attach/detach the scope unit 2 with respect to the fixed unit 3.

Additionally, there is an effect that the housings of the fixed unit 3 and the base unit 4d of the scope unit 2 can securely be fixed to each other so as to be relatively immobile by the guide pin 45 constituted as described above. Furthermore, even when the vibration or impact is applied to the fixed unit 3 and the base unit 4d of the scope unit 2, any force is not applied to the optical connector portion 17 or the connector portion 18, and therefore the optical connector portion 17 can securely be connected to the connector portion 18 without being broken.

Furthermore, connection defect can be prevented. When the whole surface is used as the abutment surface, the position is influenced by distortion of the surface, and the like. Therefore, when the tapered surface 101b of the guide pin receiving member 47 abuts on the tapered portion 45a of the guide pin 45, the guide pin 45 is positioned not only in the direction (X-Y direction) crossing at right angles to the axial direction but also in the axial direction (Z direction) of the guide pin 45. Furthermore, there is also an effect that structure is simple.

Moreover, the locking and the releasing is possible by the lock member 46 constituted as described above with the simple operation. Furthermore, the lock member is urged by the spring force of the spring member 53 at the time of the locking, and therefore there is an effect that the lock of the lock member 46 is not loosened or the connection defect is not easily caused by the vibration or impact. As a result, the housings of the fixed unit 3 and the base unit 4d of the scope unit 2 can securely be fixed to each other with the simple operation at the time of the connection, and the fixed unit 3 and the base unit 4d of the scope unit 2 can securely be fixed against the vibration or impact.

Figure 12B:
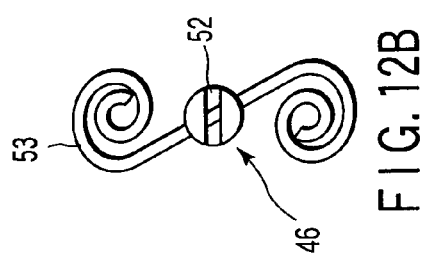
FIG. 12B is a plan view showing a fixing spring member of the fixed unit.
Figure 12C:
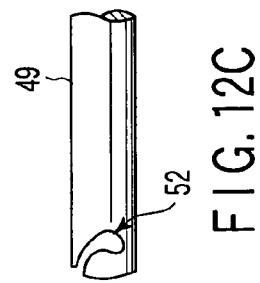
FIG. 12C is a perspective view showing a lock groove of a shaft of the fixing member.
Figure 13:
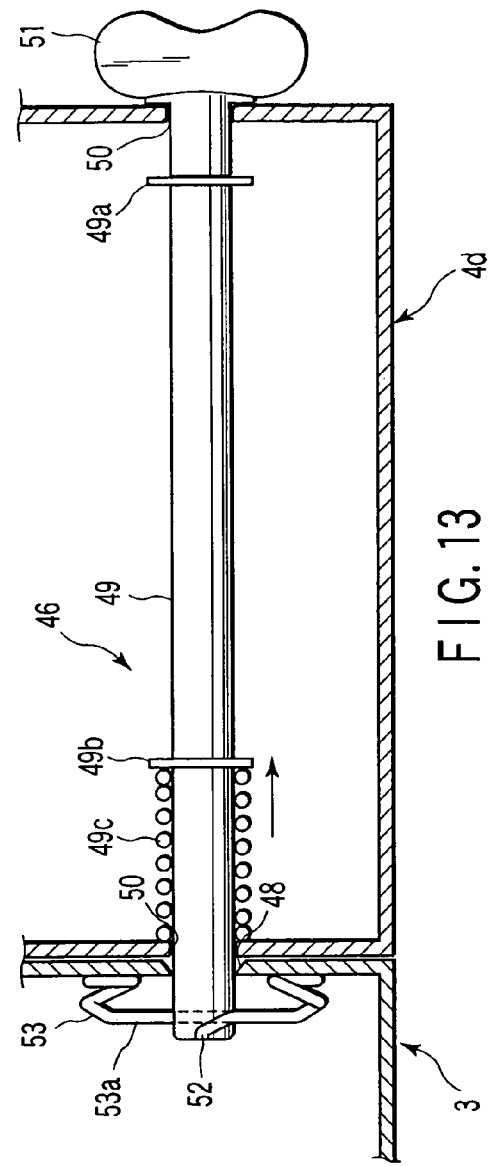
FIG. 13 is a longitudinal sectional view of a major part showing the attached state of the fixing member using an elastic member in the fixed unit and the base unit in the scope unit shown in FIG. 12.

FIG. 13 shows a modification example of the lock member in FIG. 12 described above.

A lock member 46a includes a coil spring 49c and stopper 49b for urging the shaft 49 so as to detach the shaft from the fixed unit 3 side (arrow direction).

At the time of the use of the lock member 46a, the base unit 4d of the scope unit 2 is allowed to abut on the scope unit connection surface 3b1 of the fixed unit 3. Moreover, while the knob 51 is pushed, the coil spring 49c is contracted, the engaging portion 53a of the spring member 53 is fitted into the lock groove 52 of the tip end of the shaft 49, and further the shaft 49 is pressed to rotate the knob 51. By this rotation, the engaging portion 53a of the spring member 53 is pulled into the lock groove 52 of the shaft 49, fitted into a groove bottom of the lock groove 52, and securely locked.

By this constitution, when the lock member 46 is released, the knob 51 is allowed to jump outside by the urging force of the coil spring 49c. In a state in which the knob 51 has jumped out, the operator easily grasps the knob 51. The state in which the knob 51 has jumped out corresponds to the state in which the lock is released. Therefore, visibility of a locked state/unlocked state is enhanced by presence/absence of this jump-out.

Figure 14:
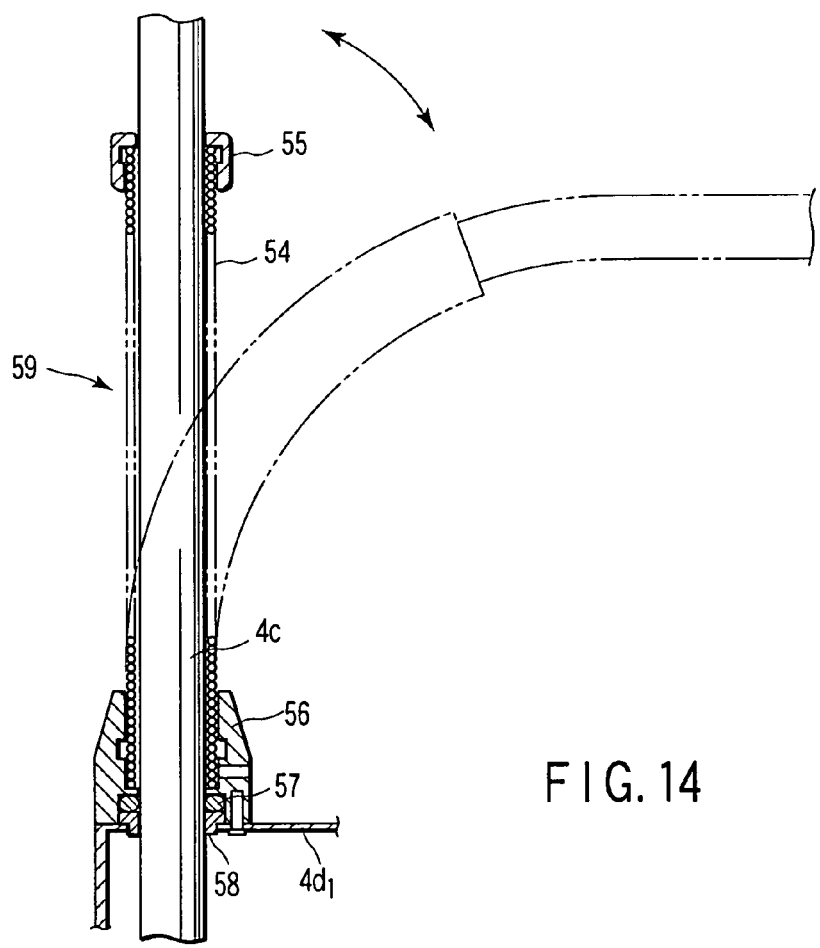
FIG. 14 is a longitudinal sectional view of a major part showing a bent stop portion of a corrugated tube in the scope unit of the first embodiment.

Moreover, FIG. 14 shows a bend stop portion 59 of the universal cable 4c disposed in the connected portion of the unit case 4d1 of the base unit 4d to the universal cable 4c. This bend stop portion 59 includes a closely wound coil 54 attached to the periphery of the universal cable 4c. The closely wound coil 54 is formed by a linear material wound in a coil shape. Moreover, the closely wound coil 54 is not excessively short or long, and has an appropriate deflection property.

Furthermore, on the tip end of the closely wound coil 54, a cap 55 is meshed and bonded so as to prevent the insertion portion 4a from being damaged by the coil end. Furthermore, a base member 56 is disposed on the base end of the closely wound coil 54. The base member 56 is fixed to the unit case 4d1 by screws from the back surface. Moreover, the base end of the closely wound coil 54 is meshed with the base member 56, and fixed by immobile screws to be prevented from loosening.

Additionally, inside the base member 56, an O ring 57 is attached so as to prevent a liquid transferred along the insertion portion 4a from entering the housing of the unit case 4d1. The O ring 57 is attached in an appropriately compressed state by an O ring press member.

The bend stop portion 59 is contained in a bent state with a small bend radius R so as to be contained in a compact manner at the time of storage of the endoscope apparatus 1. Moreover, at the time of the use of the endoscope apparatus 1, by the spring force of the closely wound coil 54, a large bend radius R, or a straight extended state shown by a solid line in FIG. 14 is obtained.

Moreover, when a corrugated tube of the universal cable 4c is pulled at the time of endoscopic inspection, as shown by a virtual line in FIG. 12, the bend stop portion 59 is bent, but returns to its original state, when a tensile force is weakened. Then, the bend stop portion 59 constituted as described above is bent to have an appropriate curvature using the closely wound coil 54, and sufficient curve capabilities can be obtained. This can solve a problem that a conventional bend stop portion molded of a rubber in a tapered shape does not return to the original state once bent or that the corrugated tube buckles or bends in the end of the bend stop portion with a hardened rubber.

Moreover, FIG. 16 is an electric system block diagram showing the schematic constitution of the inside of the fixed unit 3 and the base unit 4d in the scope unit 2 in the endoscope apparatus 1 of the present embodiment.

In the base unit 4d, power is supplied via the connector 34, and the angle and CCD control circuit 6 is disposed to transmit/receive a control signal. The angle and CCD control circuit 6 is connected to a CCD and angle driving circuit of the observation optical system of a scope (not shown) disposed on the tip-end surface of the head portion 4a 1 of the insertion portion 4a. Any of a plurality of connector connection detection signal lines 62 is grounded to GND of the circuit.

The fixed unit 3 includes a power supply circuit 8 which is connected to a commercial power supply or a DC power supply via a power supply cord (not shown) and which is constituted of a main power supply 8a and a standby power supply 8b. The main power supply 8a supplies power to the scope unit 2 via the system control circuit 10 and the connected portion of the connector 33 to the connector 34. A connector connection detection circuit 61 supplies the power from the standby power supply 8b. For the connector connection detection circuit 61, when the connector 34 is fitted with the connector 33, the connector connection detection signal lines 62 are electrically connected to the GND, and the connection of the connector 34 to the connector 33 can be detected. The system control circuit 10 exchanges a control signal with respect to the scope unit 2 via the connectors 33 and 34.

Figure 17:
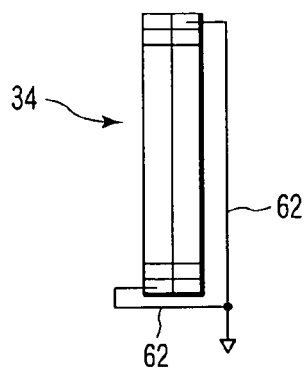
FIG. 17 is a schematic constitution diagram showing a connector detection signal line of the connector on the side of the fixed unit in the endoscope apparatus of the first embodiment.

FIG. 17 shows an arrangement example of the connector connection detection signal lines 62 in the connectors 33 and 34. Here, an example is shown in which the connector connection detection signal lines 62 are arranged in diagonal positions of connectors disposed in two columns.

Next, the function of the above-described constitution will be described. When the power supply circuit is connected to the commercial power supply or the DC power supply via the power supply cord (not shown), the power is supplied to the connector connection detection circuit 61 from the standby power supply 8b in the power supply circuit 8.

Here, when the connector 33 is incompletely connected to the connector 34, some or all of the connector connection detection signal lines 62 are not connected to the GND with respect to the connector connection detection circuit 61, and the signal line with respect to the main power supply 8a prohibits a power supply output of the main power supply 8a. Since the power supply output of the main power supply 8a is prohibited, the system control circuit 10 and the angle and CCD control circuit 6 do not operate.

When the connector 33 is completely connected to the connector 34, all of the connector detection signal lines 62 are connected to the GND with respect to the connector connection detection circuit 61, and therefore the signal line with respect to the main power supply 8a permits the power supply output of the main power supply 8a. Since the power supply output of the main power supply 8a is permitted, the system control circuit 10 and the angle and CCD control circuit 6 operate.

Furthermore, an angle of the scope unit 2 is controlled based on the control of the system control circuit 10, and the CCD on the endoscope tip end is directed in a target direction. The CCD outputs a video signal based on a driving signal of the CCD control circuit 6, and transmits the signal to the angle and CCD control circuit 6. At this time, in the angle and CCD control circuit 6, a signal by which CRT display is possible is input to the system control circuit 10 via the connectors 33 and 34. The system control circuit 10 outputs the signal to a display CRT by a cathode-ray tube or a display LCD by a color liquid crystal (not shown) so that the signal is formed into an image.

Figure 18:
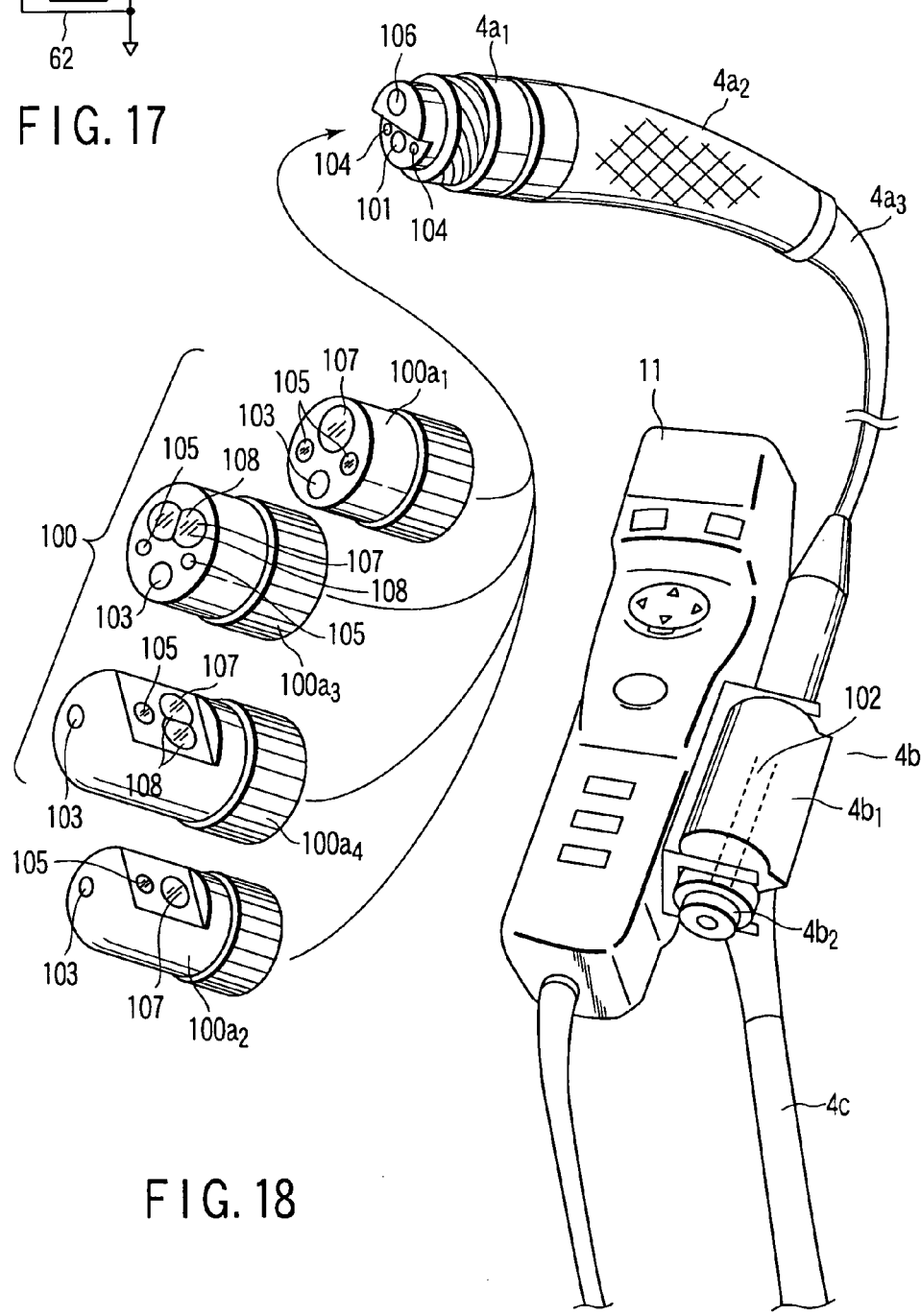
FIG. 18 is a perspective view showing a plurality of types of optical adapters connected to a tip-end surface of a head portion in the endoscope apparatus of the first embodiment.

Moreover, as shown in FIG. 18, a plurality of types of optical adapters 100 are selectively and detachably attached to the head portion 4a1 of the endoscope apparatus 1 of the present embodiment. In the optical adapters 100, for example, in addition to a direct-sight adapter 100a1 and a side-sight adapter 100a2, a direct-sight binocular adapter 100a3 for stereo measurement, and a side-sight binocular adapter 100a4 are disposed. It is to be noted that FIG. 19 is a longitudinal sectional view of the direct-sight binocular adapter 100a3 for the stereo measurement, and FIG. 20 is a longitudinal sectional view of the side-sight binocular adapter 100a4.

Each of these optical adapters 100 includes an adapter opening 103, an adapter illuminating window 105, and an observation window 107 of an adapter observation optical system. Moreover, in a state in which the optical adapters 100 is attached to the head portion 4a1 of the endoscope apparatus 1, the tip-end side opening 101, illuminating window 104, and observation window 106 of the inner channel 102 in the head portion 4a1 of the endoscope apparatus 1 are connected to the adapter opening 103 of the optical adapter 100, the adapter illuminating window 105, and the observation window 107 of the adapter observation optical system, respectively. Accordingly, the illuminative light transmitted from the light source unit 9 via the LG connector 20 is projected onto the surface of an object from the illuminating window 104 of the head portion 4a1 via the adapter illuminating window 105 in the surface of the adapter. Furthermore, the image is similarly formed in the solid image pickup device built in the head portion 4a1 from the observation window 107 of the adapter observation optical system of each adapter 100 via the observation window 106 of the observation optical system of the head portion 4a1.

Moreover, in the direct-sight binocular adapter 100a3, and side-sight binocular adapter 100a4, the observation window 107 of the adapter observation optical system includes two adapter observation windows 108 for forming the image onto one solid image pickup device in two optical paths. It is a known fact that the stereo measurement uses parallax at the time of the image formation on the solid image pickup device via the two adapter observation windows 108, and uses principle of triangulation. A constitution, function, and effect of the present invention concerning this measurement will next be described.

Furthermore, the system control circuit 10 includes a measurement function of correcting an optical strain of an endoscopic image input from the scope unit 2 to measure a dimension, area, and the like of an observation object. For the scope unit 2, scope information is input, for example, into the angle and CCD control circuit 6. The system control circuit 10 can carry out the measurement with good accuracy based on the scope information.

Then, in the above-described constitution, a part of the connectors 33 and 34 can be used to detect the connection of the scope unit 2. Moreover, it is judged by the connector connection detection signal circuit 62 whether or not the connection of the connector 33 to the connector 34 is secure, and the operation of the main power supply 8a is controlled based on a judgment result. Furthermore, endoscope information is recorded in the changeable scope unit 2, and the measurement is carried out in the system control circuit 10. Accordingly, only when the connection of the connector 33 to the connector 34 is secure, the system control circuit 10 and angle and CCD control circuit 6 can be operated, and accordingly malfunction and trouble of the circuit can be prevented in advance.

Furthermore, when the scope information indicating the type and individual piece of the scope unit 2 is recorded for each scope unit 2, the system control circuit 10 including scope information read means can adjust individual characteristics of the scope unit 2 based on the scope information at the time of execution of the measurement function, and can suppress influences of the type and individual difference of the scope unit 2 to further enhance measurement accuracy.

Moreover, in the present embodiment, the scope information for measurement is stored in the angle and CCD control circuit 6 of the scope unit 2. Here, ROM which is scope information storage means is built, for example, in the angle control circuit 6. Furthermore, in CPU of the fixed unit 3, a scope information read unit for reading the scope information, a measurement information storage unit, and a scope information comparison unit are built, respectively.

Figures 21, 22:
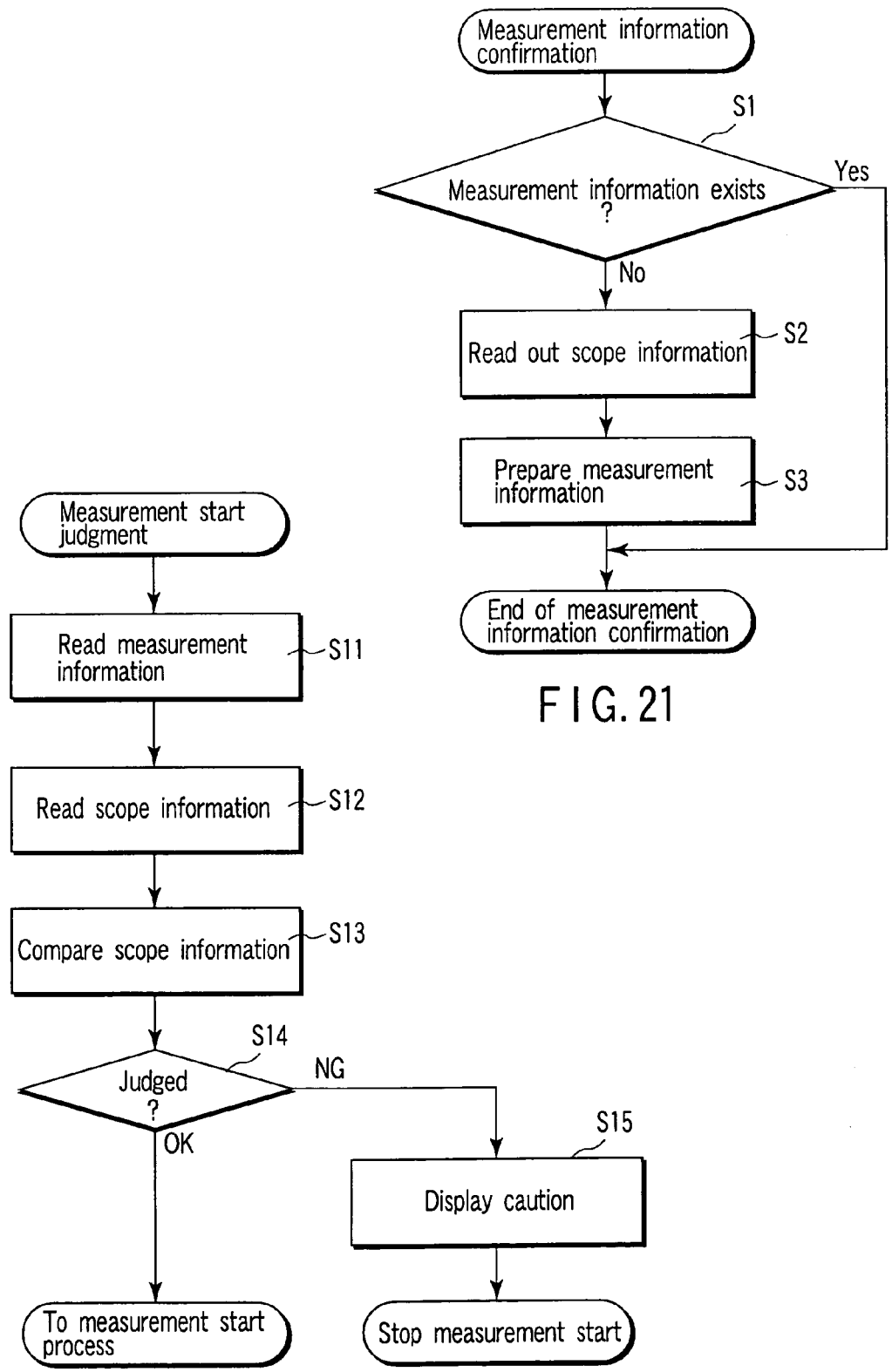
FIG. 21 is a flowchart showing an operation at a connection detection time at which the connection of the scope unit is detected in the endoscope apparatus of the first embodiment.
FIG. 22 is a flowchart showing a modification example of the operation at the connection detection time at which the connection of the scope unit is detected in the endoscope apparatus of the first embodiment.

Next, the function of the present embodiment constituted as described above will be described with reference to a flowchart for confirming the measurement information in FIG. 21, and a flowchart for judging measurement start in FIG. 22. First, in the confirmation of the measurement information, it is judged whether or not the prepared measurement information exists in a lower bond at the time of start (step S1). When it is judged in the judgment that the measurement information exists (YES), the information is not confirmed, and the process starts as such. On the other hand, when the measurement information does not exist (NO), a measurement information preparation process starts.

In the measurement information preparation process, the scope information is read out (step S2), and the measurement information is prepared in accordance with content (step S3). The scope information is constituted of a serial number, scope diameter, scope length, and scope manufacturing date. These data are also held as the measurement information. The prepared measurement information is recorded in the measurement information storage unit, and the content is held, even when the power is cut off.

Furthermore, in the measurement start judgment, the measurement information is read at the time of measurement start (step S11), and used as a parameter of the measurement. Furthermore, at this time the scope information is also read (step S12), and the scope information comparison unit compares the information with the content of the measurement information to judge whether or not there is any discrepancy (step S13). The judgment is carried out in this comparison result (step S14). When it is judged in this judgment that there is not any discrepancy (OK), the process shifts to a measurement start process as such. On the other hand, when there is the discrepancy in the comparison result (NG), it is judged that the scope unit 2 different from that at the time of the measurement information preparation is connected. In this case, a caution is given (step S15), and the measurement process is stopped.

Then, in the present embodiment constituted as described above, a change of the scope unit 2 is detected, the measurement process is not carried out with respect to the image photographed by the scope unit 2 different from that at the time of the measurement information preparation, and accordingly inaccurate measurement is prevented.

Figure 23:
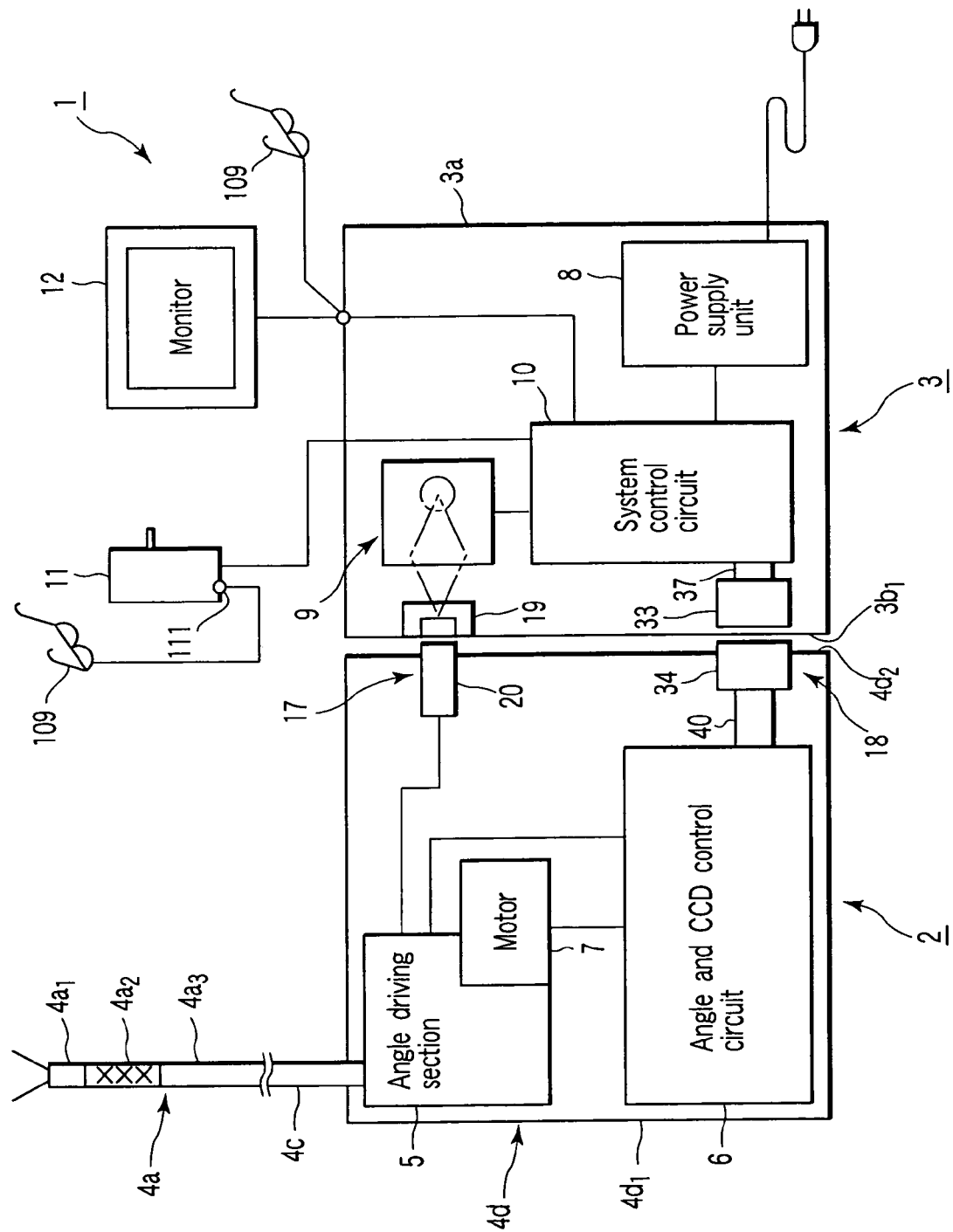
FIG. 23 is a schematic whole constitution diagram showing that three-dimensional glasses are connected to the endoscope apparatus of the first embodiment.

It is to be noted that the endoscope apparatus 1 of the present embodiment includes three-dimensional glasses 109 such as a face mount display for combined use with the direct-sight binocular adapter 100*a*3 or side-sight binocular adapter 100*a*4 as shown in FIG. 23. The glasses may also be used instead of the monitor 12 or may accessorily be used or may also be connected to a video output connector 110 of the monitor 12 or a remote controller video output connector 111 disposed in the operation remote controller 11.

Figure 24:
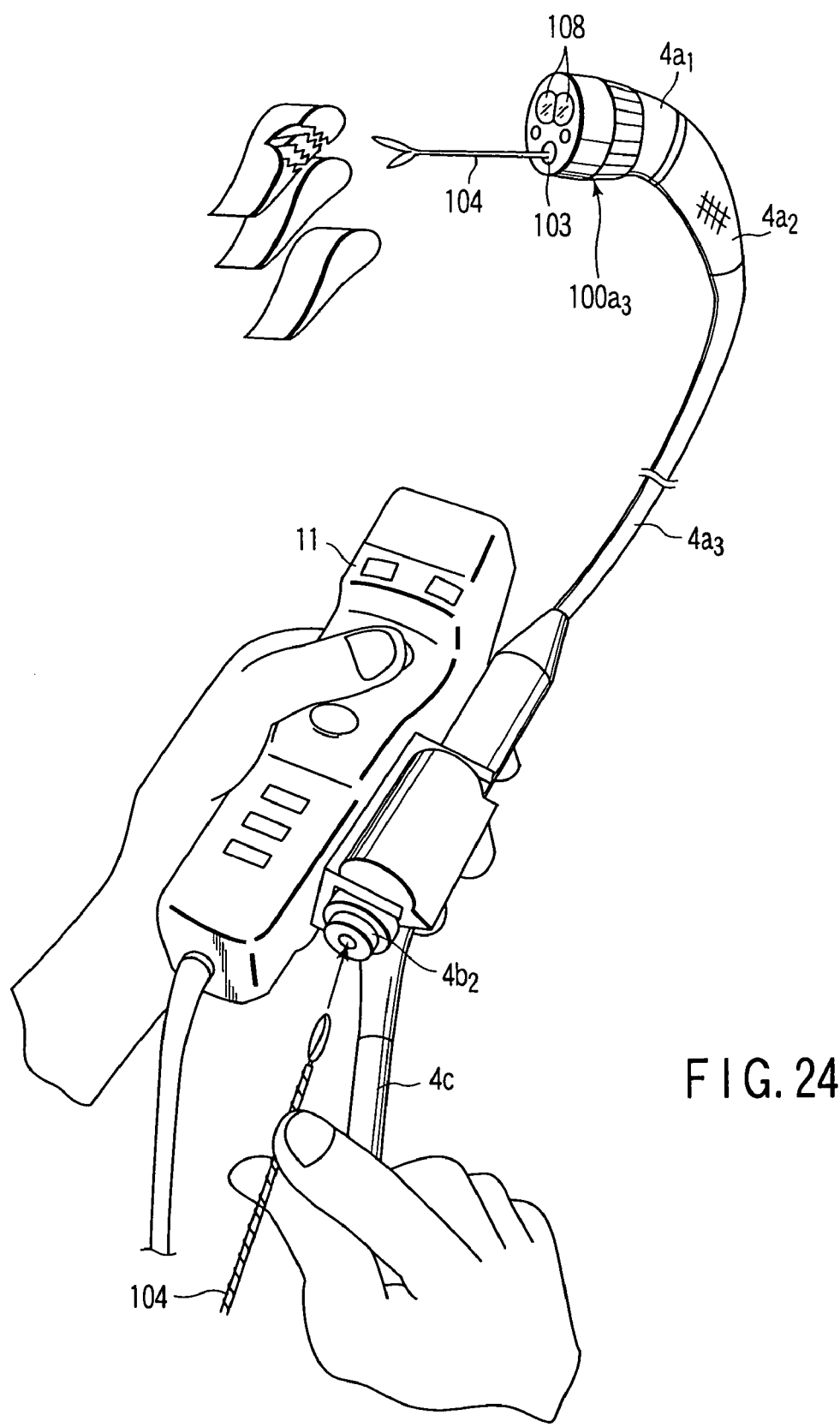
FIG. 24 is a perspective view showing an extended state of forceps from an adapter opening in a state in which the direct-sight binocular adapter is attached to a tip end of the head portion in the endoscope apparatus of the first embodiment.

In this case, the parallax of the direct-sight binocular adapter 100*a*3 or the side-sight binocular adapter 100*a*4 can be used to visually recognize a three-dimensionally displayed image, the surface of the object or the state of the position is faithfully understood, and there are effects that position visibility is enhanced and inspection efficiency increases. Furthermore, when the optical adapters 100 such as the direct-sight binocular adapter 100*a*3 are attached to the tip end of the head portion 4*a*1 as shown in FIG. 24, the position visibility of forceps 104 extended from the adapter opening 103 is also enhanced, and there is an effect that operability of the forceps 104 is enhanced.

In the present embodiment, the measurement information preparation process is executed by the endoscope apparatus 1. However, even in a constitution in which the process is executed in external processing apparatuses such as PC and the prepared measurement information is recorded in the measurement information storage unit, it is clear that the constitution is equivalent to the present embodiment.

Figure 25B:
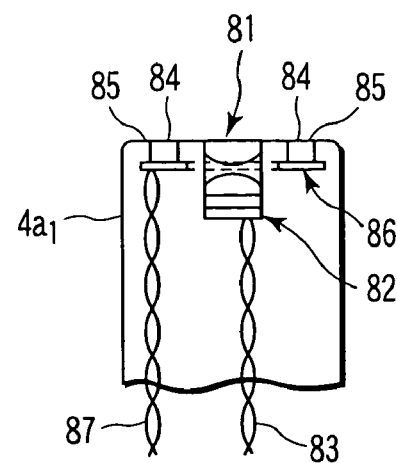
FIG. 25B is a schematic constitution diagram showing an observation unit in the tip end of an insertion portion.
Figure 25A:
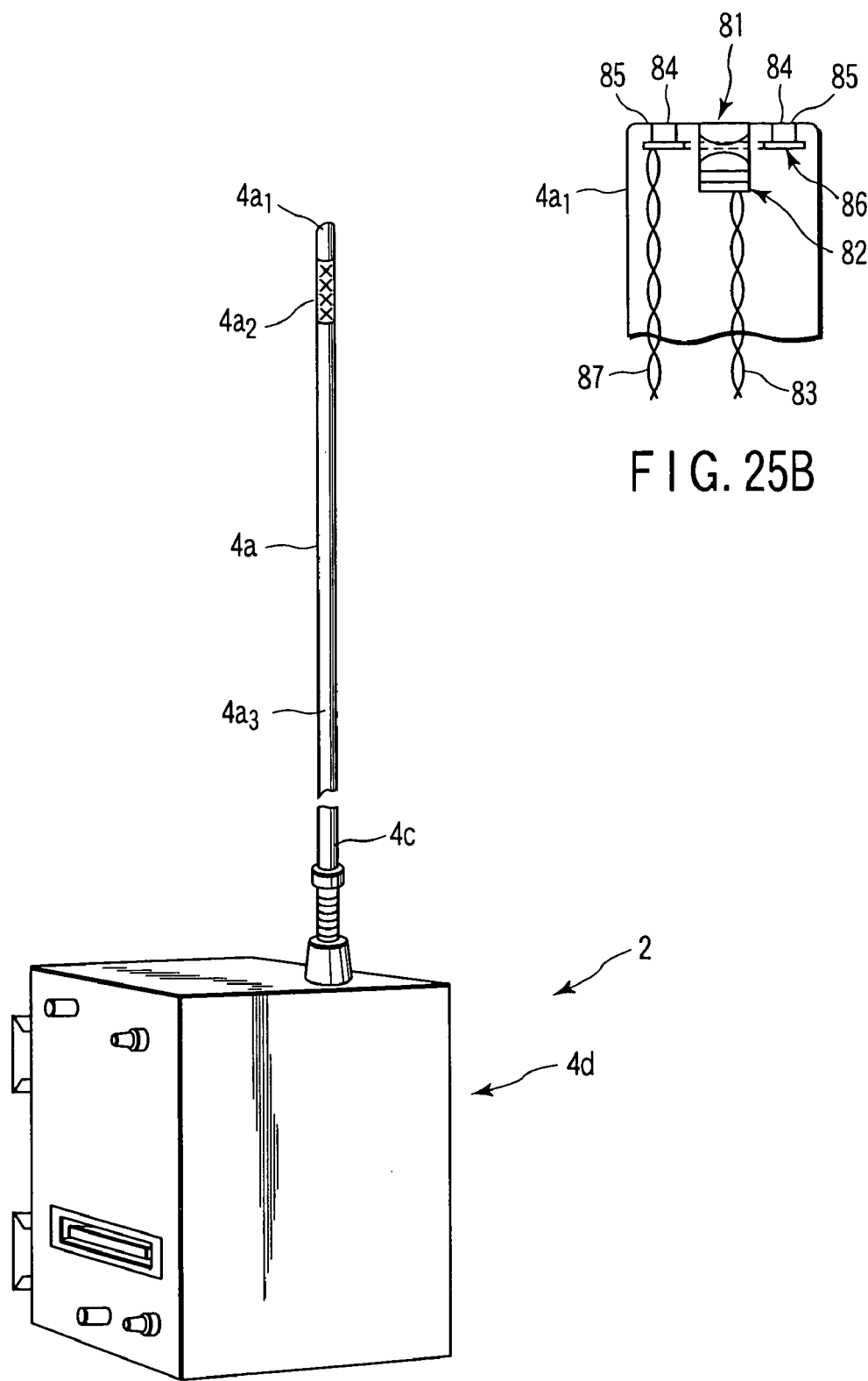
FIG. 25A is a perspective view of the scope unit in a second embodiment of the present invention.

Moreover, FIGS. 25A, 25B show a second embodiment of the present invention. In the present embodiment, the constitution of the scope unit 2 of the endoscope apparatus 1 of the first embodiment (see FIGS. 1 to 24) is changed as follows. It is to be noted that a basic constitution of the endoscope apparatus 1 of the present embodiment is substantially similar to that of the first embodiment. Therefore, the same parts as those of the first embodiment are denoted with the same reference numerals, and the description thereof is omitted.

That is, as shown in FIG. 25B, a solid image pickup device 82 of an observation optical system 81 is disposed substantially in a middle portion on the tip-end surface of the head portion 4*a*1 of the scope unit 2 of the present embodiment. The solid image pickup device 82 is connected to a camera control unit 53 via a signal line 83.

Furthermore, light emitting diodes (LED) 85 forming an illuminating unit 84 are disposed on the opposite sides of the solid image pickup device 82. Each LED 85 is disposed on a control circuit substrate 86. The control circuit substrate 86 is connected to a power supply unit 7 via a power supply cord 87. Moreover, the power is supplied to each LED 85 from the power supply unit 7 via the power supply cord 87 to emit the light.

Then, the above-described constitution produces the following effects. That is, in the endoscope apparatus 1 of the present embodiment, the LED 85 is disposed on the tip-end surface of the head portion 4*a*1 of the scope unit 2, this LED 85 is used as the light source of the illuminative light, and therefore the light source unit 9 which has been required in the first embodiment is unnecessary. Therefore, the fixed unit 3 which is an external apparatus separate from the scope unit 2 can further be miniaturized/lightened, and an attachment/detachment mechanism of the base unit 4*d* of the scope unit 2 to the fixed unit 3 can be simplified.

Figure 26:
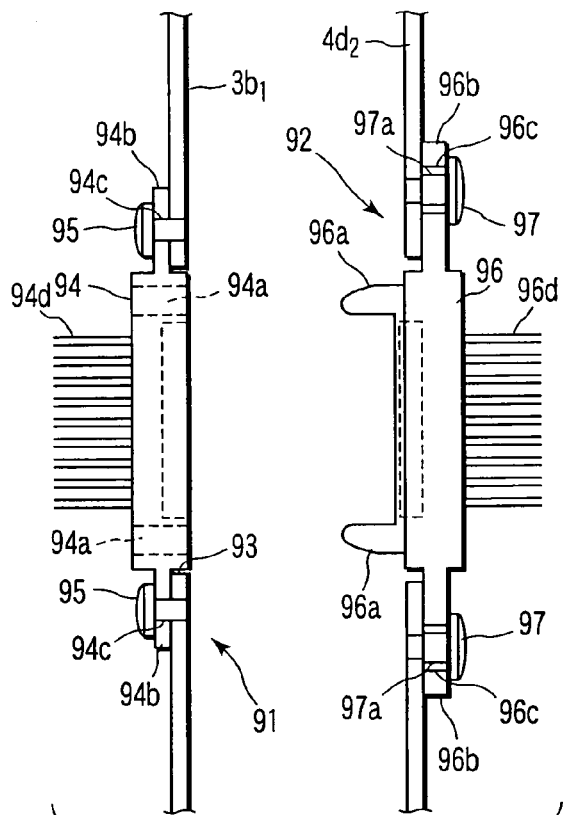
FIG. 26 is a longitudinal sectional view showing a modification example of an attaching portion of the connector of the base unit in the scope unit and that of the connector on the side of the fixed unit in the scope unit.

Moreover, FIG. 26 shows a third embodiment of the present invention. In the present embodiment, the constitutions of the connectors 33 and 34 of the endoscope apparatus 1 of the first embodiment (see FIGS. 1 to 24) are changed as follows. It is to be noted that the basic constitution of the endoscope apparatus 1 of the present embodiment is substantially similar to that of the first embodiment. Therefore, the same parts as those of the first embodiment are denoted with the same reference numerals, and the description thereof is omitted.

That is, a fixed unit side connector 91 is directly attached to the scope unit connection surface 3*b*1 of the fixed unit 3 in the present embodiment. Here, a connector mounting hole 93 is formed in the scope unit connection surface 3*b*1 of the fixed unit 3. A main body 94 of the fixed unit side connector 91 is disposed in the connector mounting hole 93.

Connector concave portions 94*a* for the positioning are disposed in the opposite ends of the connector main body 94. Furthermore, protrusions 94*b* for attachment are disposed on the opposite sides of the connector main body 94. A screw insertion hole 94c is formed in each protrusion 94b. Moreover, the protrusion 94b of the connector main body 94 is fixed to the scope unit connection surface 3b1 of the fixed unit 3 by a fixing screw 95 with the high positional accuracy.

Moreover, one end of a harness 94d is connected to the connector main body 94 of the fixed unit 3. The other end of the harness 94d is connected to the system control circuit 10 in the fixed unit 3.

Furthermore, a scope side connector 92 is directly attached to the end plate 4d2 of the unit case 4d1 of the scope unit 2. Here, a connector mounting hole is formed in the end plate 4d2 of the unit case 4d1. A main body 96 of the scope unit side connector 9 is disposed in this connector mounting hole.

Connector convex portions 96a for the positioning are disposed on the opposite ends of the connector main body 96. Furthermore, protrusions 96b for attachment are disposed on the opposite sides of the connector main body 96. A screw hole 96c having a diameter larger than that of a screw portion 97b of a fixing screw 97 is formed in each protrusion 96b. A gap between the screw hole 96c of the connector main body 96 and a screw portion 97a is disposed as a play portion 98 which permits the backlash at the time of the connection. This play portion 98 is disposed, and the electric connector main body 96 is attached to the end plate 4d2 of the unit case 4d1 by the fixing screw 97. The backlash at the time of the connection is permitted, the positioning can easily be carried out, and the attaching can be carried out.

Moreover, the connector main body 96 is connected to one end of a harness 96d. The other end of this harness 96d is connected to the angle and CCD control circuit 6 in the scope unit 2.

Furthermore, when the connector convex portions 96a of the opposite ends of the connector main body 96 are fitted into two connector concave portions 94a of the fixed unit side connector 91, respectively, at the time of the connection of the fixed unit side connector 91 to the scope side connector 92, the axial alignment is carried out so that the positions of the connector convex portions 96a of the opposite ends of the main body 96 are determined in accordance with those of the connector concave portions 94a.

Furthermore, at the time of the connection of the fixed unit side connector 91 to the scope side connector 92, the connector main body 96 moves in the range of the gap between a large-diameter hole 98 of the protrusion 96b and the fixing screw 97, and accordingly the connector convex portions 96a are inserted into and are smoothly coupled to the connector concave portions 94a.

Then, in the present embodiment, the substrate 36 of the connector 33 of the first embodiment, and the substrate 39 of the connector 34 are not required, and therefore there is an effect that the constitution can be simplified.

It is to be noted that the present invention is not limited to the above-described embodiments. For example, the connecting portion of the fixed unit 3 to the scope unit 2 is not limited to the optical connector for the illuminative light or the connector for the signal. For example, a connector for a fluid may also be used, and the connecting portion is not limited as long as the base unit 4d is detachably connected to the fixed unit 3 and the connecting portion is required for substantially functioning as the endoscope apparatus and is mechanical.

Figure 27:
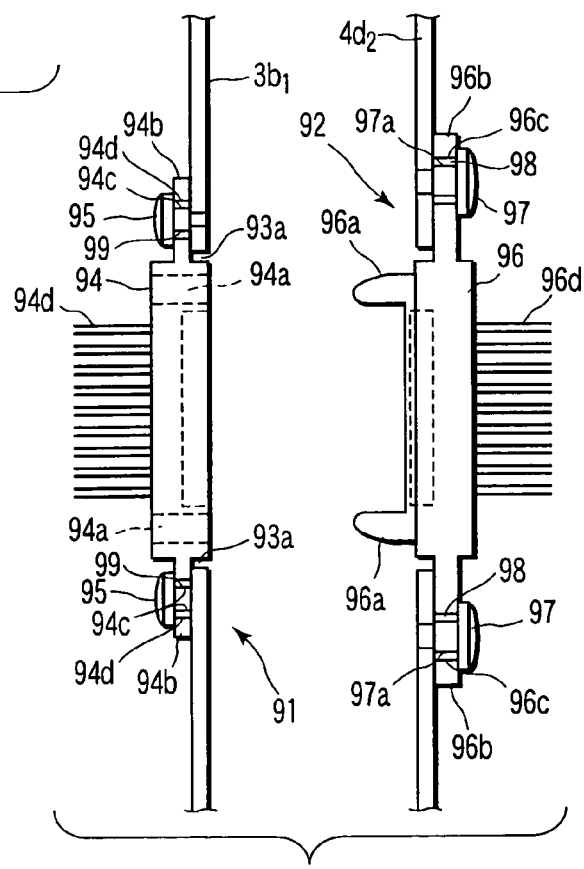
FIG. 27 is a longitudinal sectional view showing a modification example of the attaching portion of the connector of the base unit in the scope unit shown in FIG. 26 and that of the connector on the side of the fixed unit in the scope unit.

FIG. 27 shows a modification example of the third embodiment.

In the above-described third embodiment, the play portion 98 at the time of the attaching of the scope side connector 92 to the end plate 4d2 of the unit case 4d1 is disposed, but in this modification example, a play portion 99 also at the time of the fixing of the connector main body 94 to the scope unit connection surface 3b1 is disposed.

A bore diameter of the screw insertion hole 94c on the connector main body 94 side is formed to be larger than the diameter of the screw portion of the fixing screw 95, and a gap between the screw portion and the screw insertion hole 94c is disposed as the play portion 99. By this constitution, when the connector main body 94 is fixed to the scope unit connection surface 3b1 by the fixing screw 95, the backlash is disposed in the connector main body 94 by the range of the play portion 99.

By this constitution, since the play portion 98 of the connector main body 96 and the play portion 99 of the connector main body 94 are disposed, accordingly the deviation width permitted at the attachment time increases, and the positioning in the attachment operation by the operator is facilitated.

Figure 28:
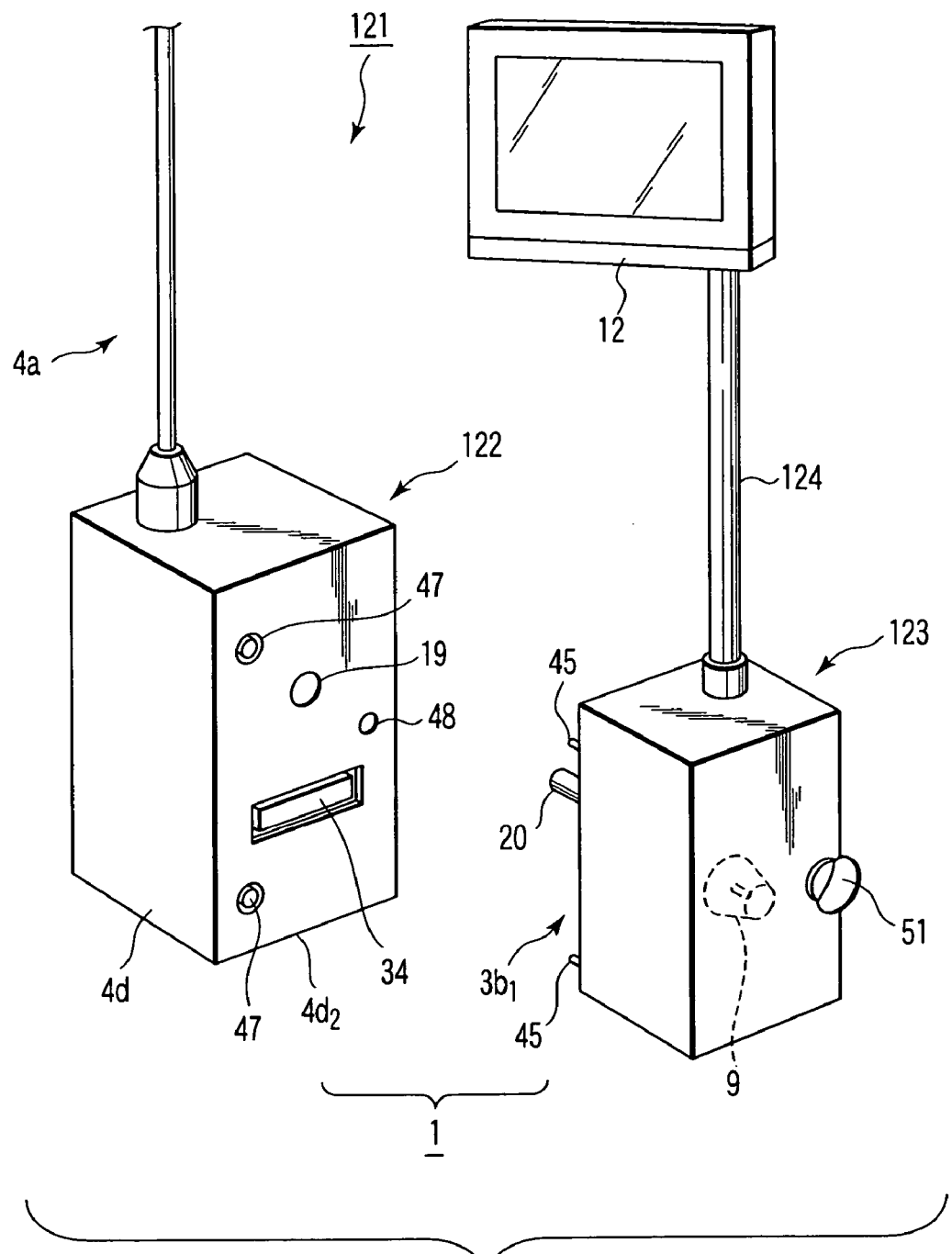
FIG. 28 is an explanatory view of connection of the scope unit to the fixed unit in the endoscope apparatus of a fourth embodiment.

FIG. 28 shows a fourth embodiment. In the above-described first embodiment, the scope unit 2 of the endoscope apparatus 1 is connected to the fixed unit 3 via two planes crossing at right angles to each other, including one plane by the scope unit connection surface 3b1 and the end plate 4d2 of the base unit 4d and one plane obtained by fitting the guide rail 14 into the slider member 13 to be slid.

In the present embodiment, since the apparatus is simplified, lightened, and miniaturized, the guide rail and slider member do not have to be necessarily used to connect the unit to the other unit. In the present embodiment and embodiments described hereinafter, the connection by one plane constituted of the scope unit connection surface 3b1 and the end plate 4d2 of the base unit 4d is realized. It is to be noted that the basic constitution of the endoscope apparatus 1 of the present embodiment is constituted using substantially the same members as those of the first embodiment in different arrangement. Therefore, the same members are denoted with the same reference numerals as those of the first embodiment, and the description thereof is omitted.

A fixed unit 123 of the present embodiment mainly includes the light source unit 9, LG connector 20, knob 51 of the lock member 46 (not shown), connector 33 (not shown), monitor 12, and guide pin 45. Among these, the LG connector 20, the connector 33, and a plurality of (two herein) guide pins 45 are arranged on the scope unit connection surface 3b1 of the fixed unit 123.

On the other hand, a scope unit 122 mainly includes the insertion portion 4a and base unit 4d, and the base unit 4d includes the light source side optical connector 19, connector 34, guide pin receiving member 47, and lock hole 48.

To connect the fixed unit 123 to the scope unit 122, the end plate 4d2 is brought close to the scope unit connection surface 3b1, and the axial alignment of the light source side optical connector 19 with the LG connector 20 is carried out. Since the play portions are disposed in these as described above, the axial alignment can relatively easily be carried out, and further the guide pin 45 is pushed forward and fitted into the guide pin receiving member 47. Thereafter, the connector 34 is fitted with the connector 33 (not shown) to achieve the electric connection. Furthermore, after the end plate 4d2 abuts on the scope unit connection surface 3b1, the knob 51 is rotated to fix the lock member into the lock hole 48. Accordingly, the connection of the fixed unit 123 to the scope unit 122 is completed.

Figure 29:
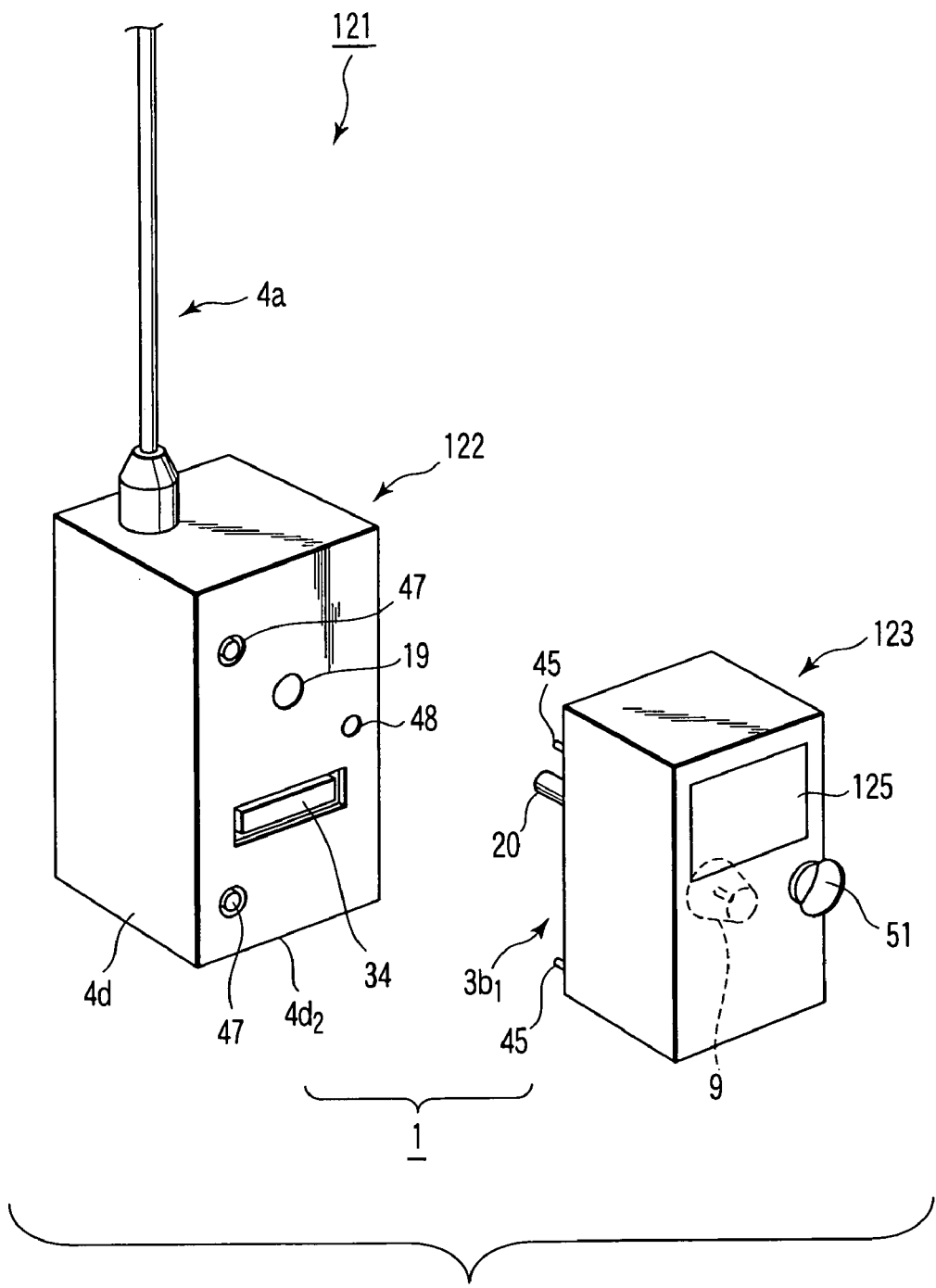
FIG. 29 is a diagram showing a modification example in the endoscope apparatus of the fourth embodiment.

FIG. 29 shows a modification example of the fourth embodiment.

The monitor 12 of the fixed unit 123 in the above-described fourth embodiment shows an example in which a frame (pipe) 124 is used to constitute the monitor separately from the fixed unit main body, but this modification example is an example in which the monitor is disposed as a built-in monitor 124 in the fixed unit 123 main body. When the monitor 12 is built in the fixed unit main body, the fixed unit can be miniaturized, and is easily carried. Since the built-in monitor 124 is disposed, center of gravity of the fixed unit 123 is lowered to improve balance, and the connection operation with respect to the scope unit 122 is facilitated.

Figure 30:
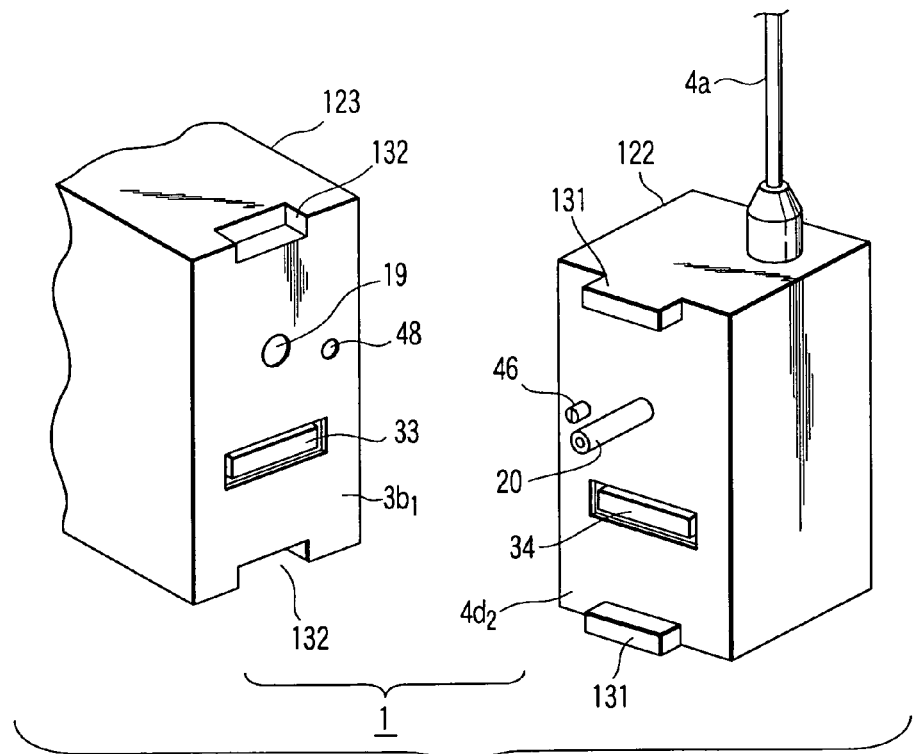
FIG. 30 is an explanatory view of the connection of the scope unit to the fixed unit in the endoscope apparatus of a fifth embodiment.

FIG. 30 shows a fifth embodiment.

In the present embodiment, shapes of the above-described guide pin 45 and guide pin receiving member 47 are changed. It is to be noted that the basic constitution of the endoscope apparatus in the present embodiment is substantially similar to that of the above-described fourth embodiment, the same members are denoted with the same reference numerals as those of the fourth embodiment, and the description thereof is omitted.

In the present embodiment, on upper and lower ends of the end plate 4d2 of the scope unit 122, positioning convex portions 131 having rectangular shapes are disposed to extend over upper and lower surfaces, and in the upper and lower ends of the scope unit connection surface 3b1 of the fixed unit 123, positioning concave portions 132 agreeing with the positioning convex portions 131 are disposed to extend over the upper and lower surfaces. A connection procedure in this embodiment is similar to that of the above-described fourth embodiment. It is to be noted that the shapes of the positioning concave/convex portions are not limited to the rectangular shapes, and can be various. For example, semicircular shapes may also be used.

When the positioning convex portions 131 and positioning concave portions 132 are disposed, the high positional accuracy can be obtained with the simple structure at the connection time.

Figure 31:
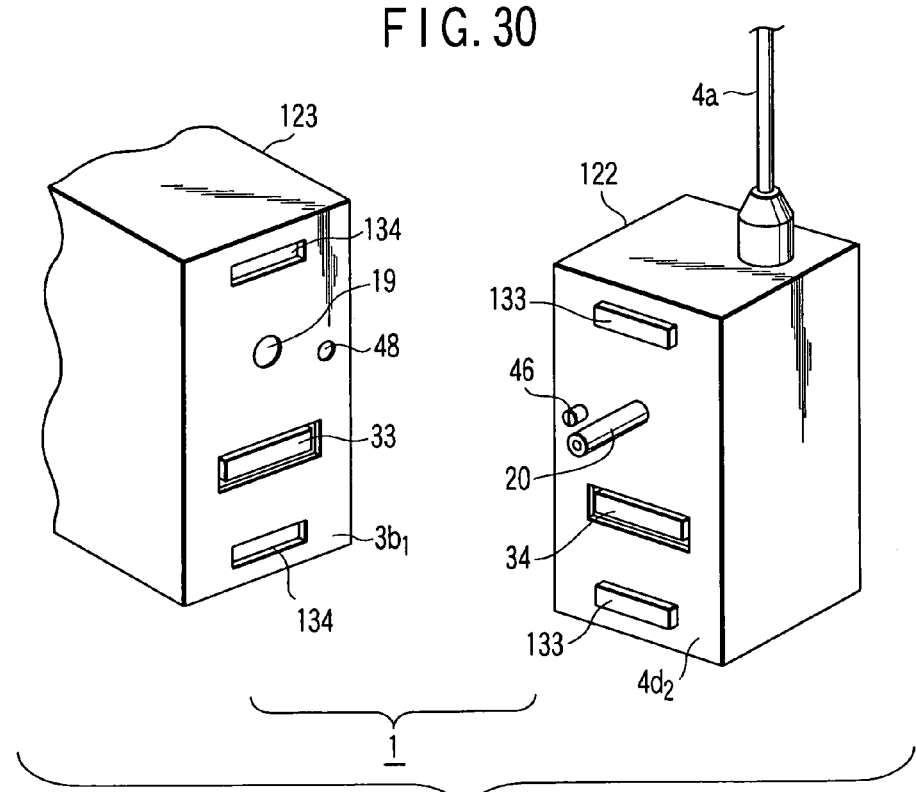
FIG. 31 is a diagram showing a first modification example in the endoscope apparatus of the fifth embodiment.

FIG. 31 shows a first modification example of the above-described fifth embodiment.

The positioning convex/concave portions are disposed with respect to the upper and lower surfaces in the fifth embodiment, but in the present modification example, positioning convex portions 133 having the rectangular shapes are disposed on the upper and lower sides within the surface of the end plate 4d2. On the other hand, positioning concave portions 134 agreeing with the positioning convex portions 133 are disposed on the upper and lower sides within the plane of the scope unit connection surface 3b1. It is to be noted that the shapes of the positioning concave/convex portions are not limited to the rectangular shapes, and can be various. For example, semispherical shapes, circular cylindrical shapes, or polygonal shapes may also be used.

Also in this modification example, when the positioning convex portions 133 and positioning concave portions 134 are disposed, the high positional accuracy can be obtained with the simple structure at the connection time.

Figure 32:
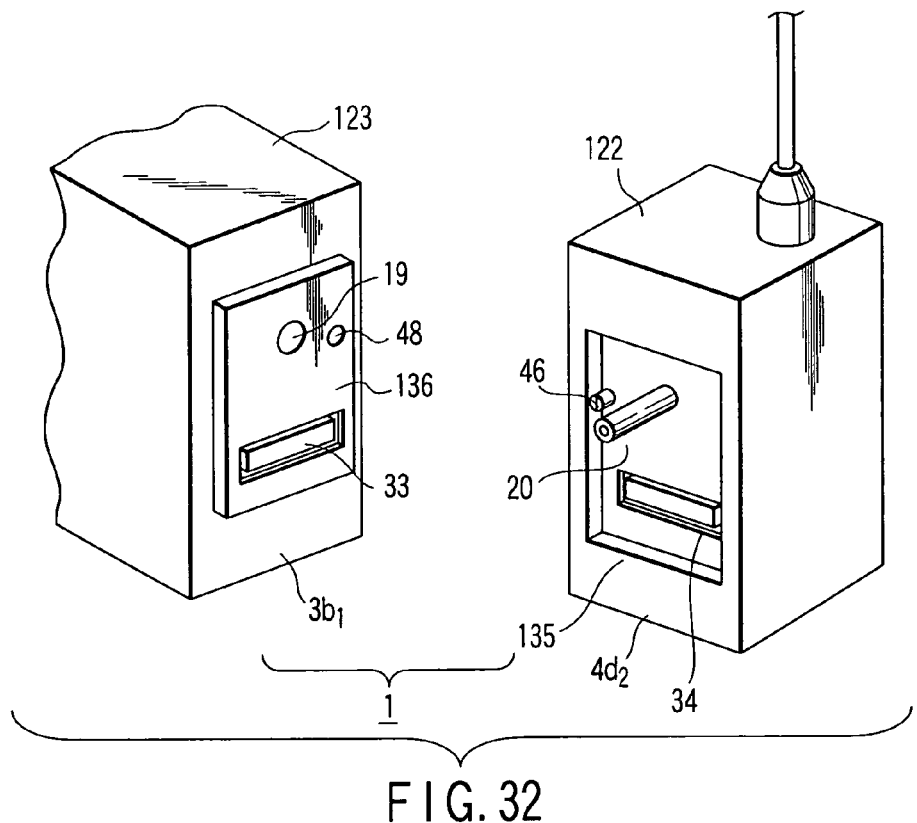
FIG. 32 is a diagram showing a second modification example in the endoscope apparatus of the fifth embodiment.

FIG. 32 shows a second modification example of the above-described fifth embodiment.

In the modification example, in the scope unit connection surface 3b1, a plane including the light source side optical connector 19, connector 33, and lock hole 48 is formed as a positioning convex surface 136 to be higher by one step. Moreover, to fit with the positioning convex surface 136, a positioning concave surface 137 is formed on the side-of the plane of the end plate 4d2. Also in this modification example, the positioning convex surface 136 and positioning concave surface 137 are disposed, and accordingly the high positional accuracy can be obtained with the simple structure at the connection time.

Figure 33:
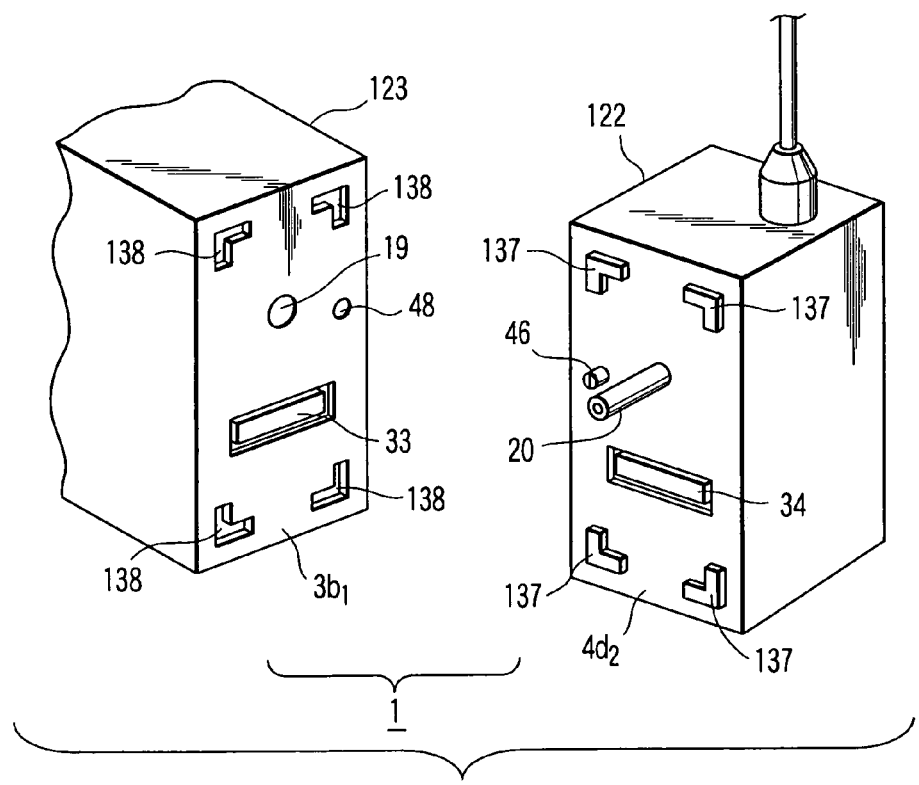
FIG. 33 is a diagram showing a third modification example in the endoscope apparatus of the fifth embodiment.

FIG. 33 shows a third modification example of the above-described fifth embodiment.

In the present modification example, positioning L-shaped convex portions 137 having L shapes are disposed on four corners including upper left/right and lower left/right corners within the plane of the end plate 4d2. On the other hand, positioning L-shaped concave portions 138 agreeing with the positioning L-shaped convex portions 137 are disposed in the upper left/right and lower left/right corners within the plane of the scope unit connection surface 3b1. Even in this modification example, the positioning L-shaped convex portions 137 and positioning L-shaped concave portions 138 are disposed, and accordingly the high positional accuracy can be obtained with the simple structure at the connection time.

Figure 34:
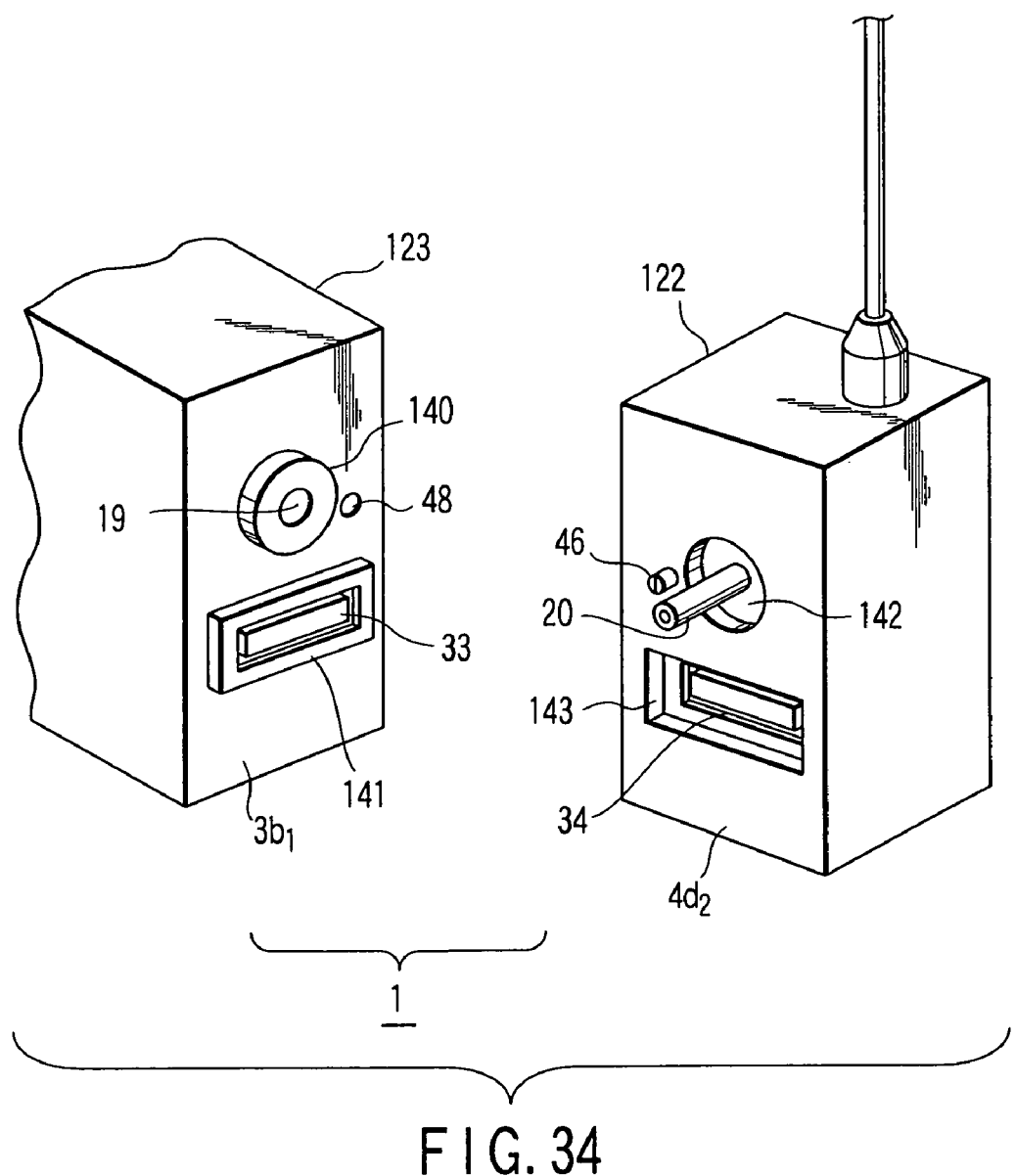
FIG. 34 is a diagram showing a fourth modification example in the endoscope apparatus of the fifth embodiment.

FIG. 34 shows a fourth modification example of the above-described fifth embodiment.

In the present modification example, a positioning annular (donut-shaped) convex portion 140 is disposed around the light source side optical connector 19 within the plane of the scope unit connection surface 3b1, and a positioning frame-shaped convex portion 141 is disposed around the connector 33. A positioning annular concave portion 142 to be fitted with the positioning annular convex portion 140 is disposed around the LG connector 20 of the end plate 4d2, and a positioning frame-shaped concave portion 143 to be fitted with the positioning frame-shaped convex portion 141 is disposed around the connector 34. Even in this modification example, the convex portions 140, 141 and concave portions 142, 143 are disposed, and accordingly the high positional accuracy can be obtained with the simple structure at the connection time.

Figure 35:
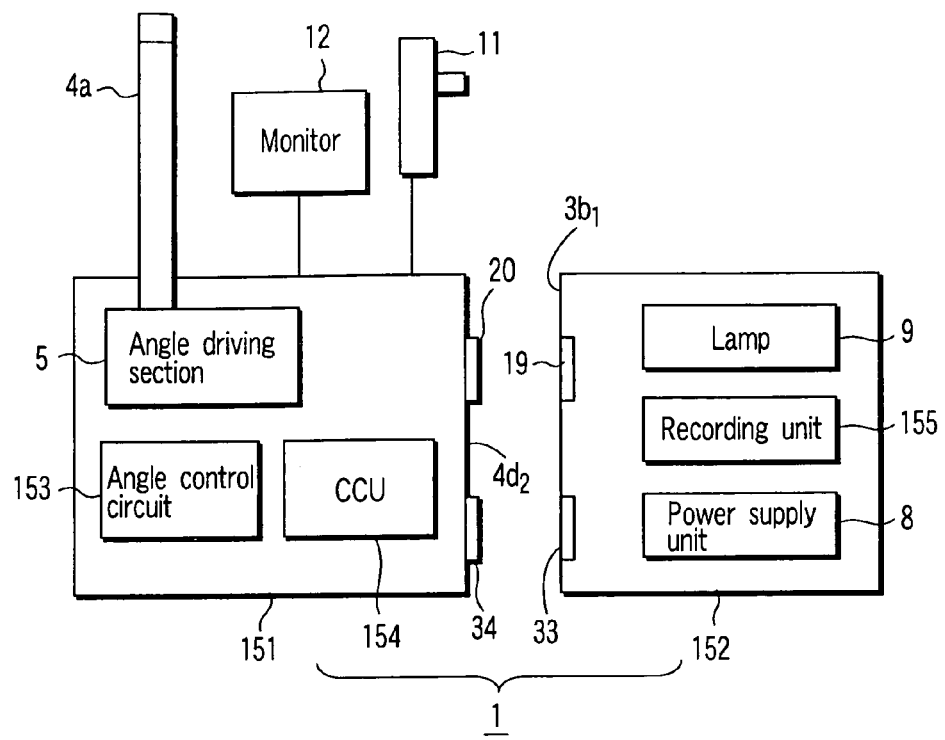
FIG. 35 is an explanatory view of a combination of constituting portions of the scope unit and fixed unit in the endoscope apparatus of a sixth embodiment.

FIG. 35 shows a sixth embodiment.

In the constitution shown in FIG. 1 described above, the constituting members are disposed in the scope unit 2 and fixed unit 3 of the endoscope apparatus 1, but the constitution is not limited to this, and various combinations can be obtained. These constituting members will be described in accordance with a combination example mounted on the scope unit 2 and fixed unit 3. To hereinafter distinguish the scope unit from the fixed unit, a unit in which the insertion portion 4a is disposed will be referred to as the scope unit, and the other unit will be referred to as the fixed unit. It is to be noted that for the constituting members of the present embodiment, the constituting members equivalent to those shown in FIG. 1 are denoted with the same reference numerals.

As shown in FIG. 35, the endoscope apparatus 1 is constituted of a scope unit 151 and fixed unit 152.

In the scope unit 151, the insertion portion 4a, angle driving section 5, angle control circuit 153, camera control unit (CCU) 154, LCD monitor 12, and operation remote controller 11 are disposed. In the end plate 4d2 of the scope unit 151, the LG connector 20 and connector 34 are disposed.

On the other hand, in the fixed unit 152, the lamp 9, power supply unit 8, and recording unit 155 in which information such as image data and numeric values concerning the data is recorded are disposed. As the recording unit 155, a recording apparatus having a relatively large storage capacity is required, and a semiconductor memory apparatus (RAM, and the like), hard disk (HDD), magneto-optical disk drive, and the like are preferable. Also in the scope unit connection surface 3b1, the light source side optical connector 19 and connector 33 are arranged.

By this constitution, a plurality of types of peripheral apparatuses (fixed units) including different specifications such as the lamp 9 and recording unit 155 are prepared, and can be changed in accordance with use purposes or specimens.

Figure 36:
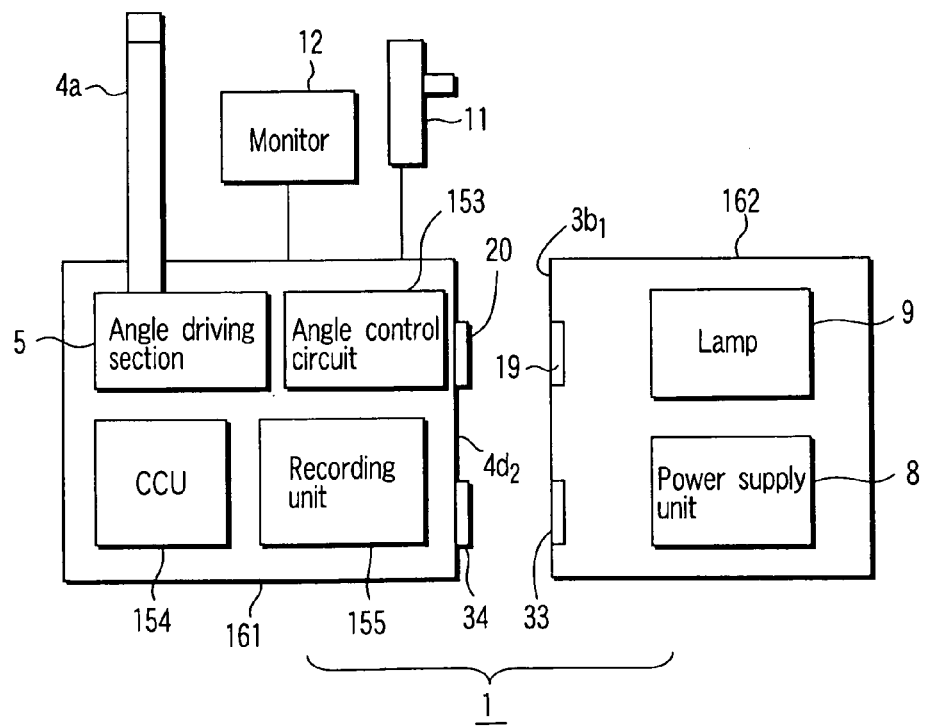
FIG. 36 is a diagram showing a first modification example in the endoscope apparatus of the sixth embodiment.

FIG. 36 shows a first modification example of the sixth embodiment.

The endoscope apparatus 1 of the present modification example is constituted of a scope unit 161 and fixed unit 162. The recording unit 155 in the sixth embodiment is moved to the scope unit 151 from the fixed unit 152 in this example.

Therefore, in a scope unit 161, the insertion portion 4a, angle driving section 5, angle control circuit 153, camera control unit (CCU) 154, LCD monitor 12, operation remote controller 11, and recording unit 155 are arranged. In the end plate 4d2 of the scope unit 151, the LG connector 20 and connector 34 are arranged.

On the other hand, in the fixed unit 152, the lamp 9 and power supply unit 8 are arranged. Further in the scope unit connection surface 3b1, the light source side optical connector 19 and connector 33 are arranged.

By this constitution, a plurality of fixed units (light source units) on which the lamps 9 having different from light amounts are mounted are prepared, and accordingly a fixed unit having a large light amount, a small-sized fixed unit, and the like can be selected and changed in accordance with the use purpose or specimen.

Figure 37:
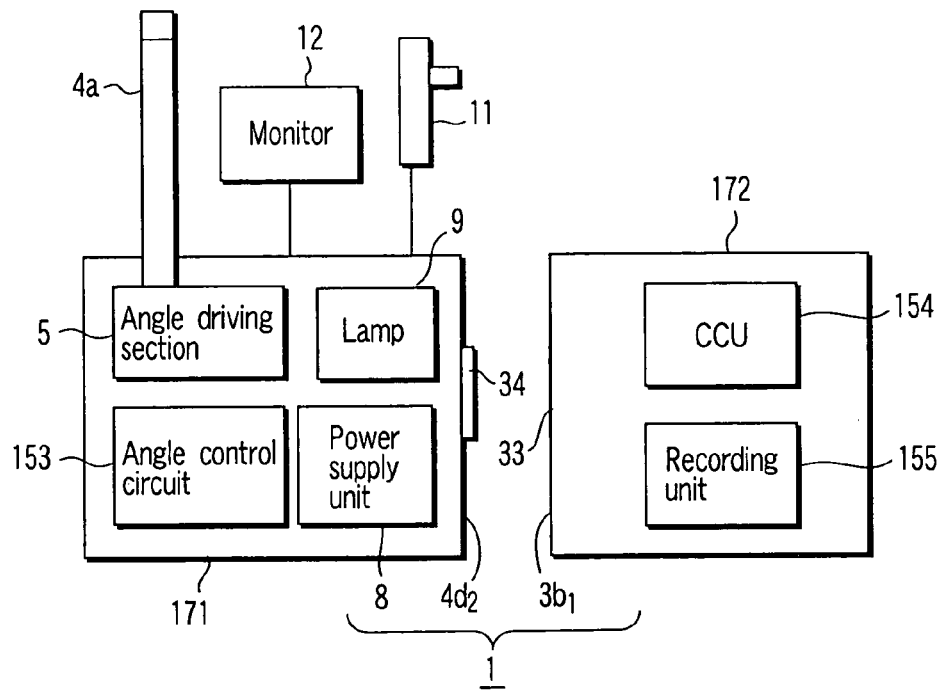
FIG. 37 is a diagram showing a second modification example in the endoscope apparatus of the sixth embodiment.

FIG. 37 shows a second modification example of the sixth embodiment.

The endoscope apparatus 1 of the present modification example is constituted of a scope unit 171 and fixed unit 172. In this fixed unit 172, the CCU 154 and recording unit 155 are arranged. On the scope unit connection surface 3b1, only the connector 33 is disposed.

Moreover, in the scope unit 171, the insertion portion 4a, angle driving section 5, angle control circuit 153, power supply unit 8, lamp 9, operation remote controller 11, and LCD monitor 12 are arranged. Further on the end plate 4d2 of the scope unit 151, only the connector 34 is disposed.

In this modification example, in the fixed unit 172, the CCU 154 and recording unit 155 are arranged, image processing and image recording are thus constituted as separate units, and the fixed unit may be prepared in accordance with the photographed image or the capability of the image processing. In future, the constitution can be upgraded with respect to the fixed unit whose processing capability of a further sophisticated image increases.

Figure 38:
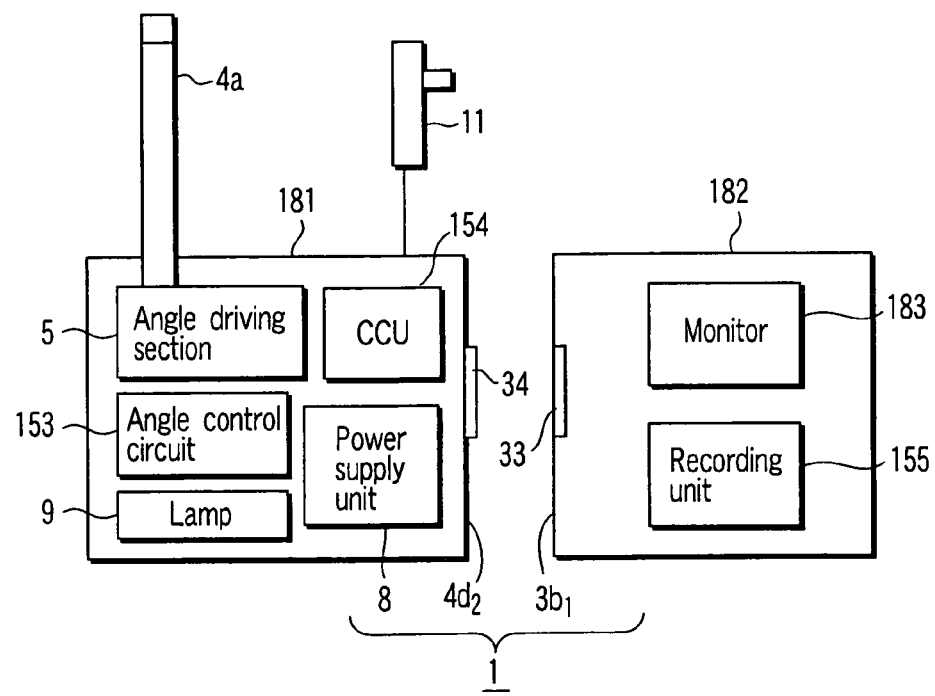
FIG. 38 is a diagram showing a third modification example in the endoscope apparatus of the sixth embodiment.

FIG. 38 shows a third modification example of the sixth embodiment.

The endoscope apparatus 1 of the present modification example is constituted of a scope unit 181 and fixed unit 182. In the present modification example, the CCU 154 and monitor 12 in the above-described second modification example are changed in the constitution.

In the scope unit 181, the insertion portion 4a, angle driving section 5, angle control circuit 153, power supply unit 8, lamp 9, and operation remote controller 11 are arranged. Further on the end plate 4d2 of the scope unit 151, only the connector 34 is disposed. On the other hand, in the fixed unit 182, a built-in type monitor 183 and recording unit 155 are arranged. On the scope unit connection surface 3b1, only the connector 33 is disposed.

In this modification example, the constituting portions associated with the image, such as the monitor 183 and recording unit 155, are arranged in the fixed unit. Therefore, assuming that the monitor 183 is a liquid crystal display and the recording unit 155 is a semiconductor memory, a large-scaled miniaturization and capability enhancement can be achieved in Figure, the constitution can also variously be changed in accordance with the use purpose, and the upgrading is also facilitated.

Figure 39:
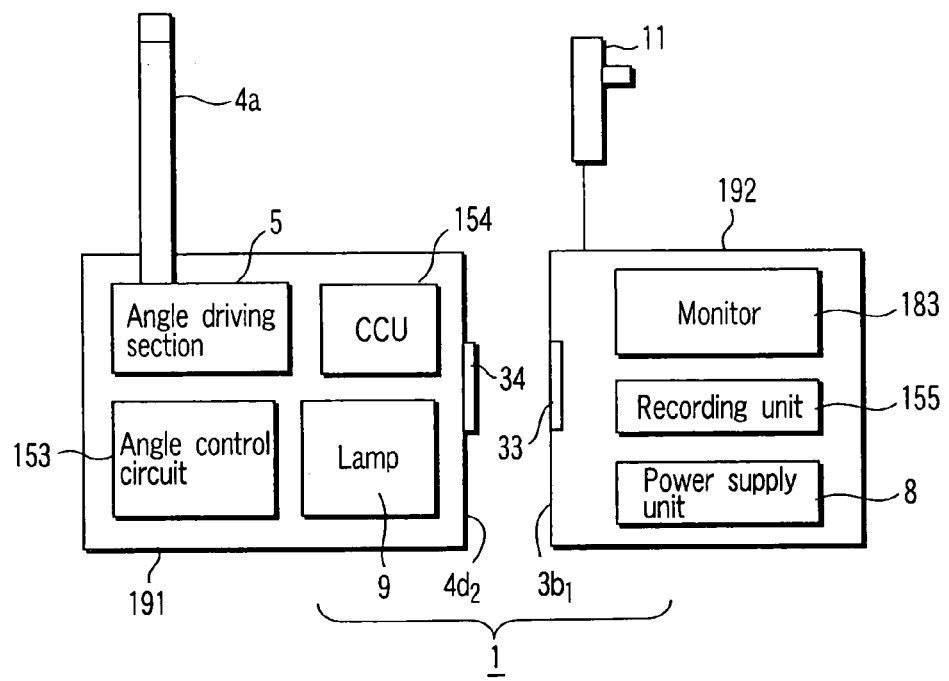
FIG. 39 is a diagram showing a fourth modification example in the endoscope apparatus of the sixth embodiment.

FIG. 39 shows a fourth modification example of the sixth embodiment.

The endoscope apparatus 1 of the present modification example is constituted of a scope unit 191 and fixed unit 192. In this modification example, the power supply unit 8 and operation remote controller 11 of the scope unit 181 in the above-described third modification example are moved to the fixed unit 192 in the constitution.

That is, in the scope unit 191, the insertion portion 4a, angle driving section 5, angle control circuit 153, lamp 9, and CCU 154 are arranged. Moreover, on the end plate 4d2 of the scope unit 151, only the connector 34 is disposed. On the other hand, in the fixed unit 182, the built-in type monitor 183, recording unit 155, power supply unit 8, and operation remote controller 11 are arranged. Only the connector 33 is disposed on the scope unit connection surface 3b1.

In this modification example, a plurality of types of scope units 191 including different specifications such as an insertion length of the insertion portion 4a, outer diameter, and light amount are prepared, and accordingly the units can be changed and used in accordance with the use purpose.

Figure 40:
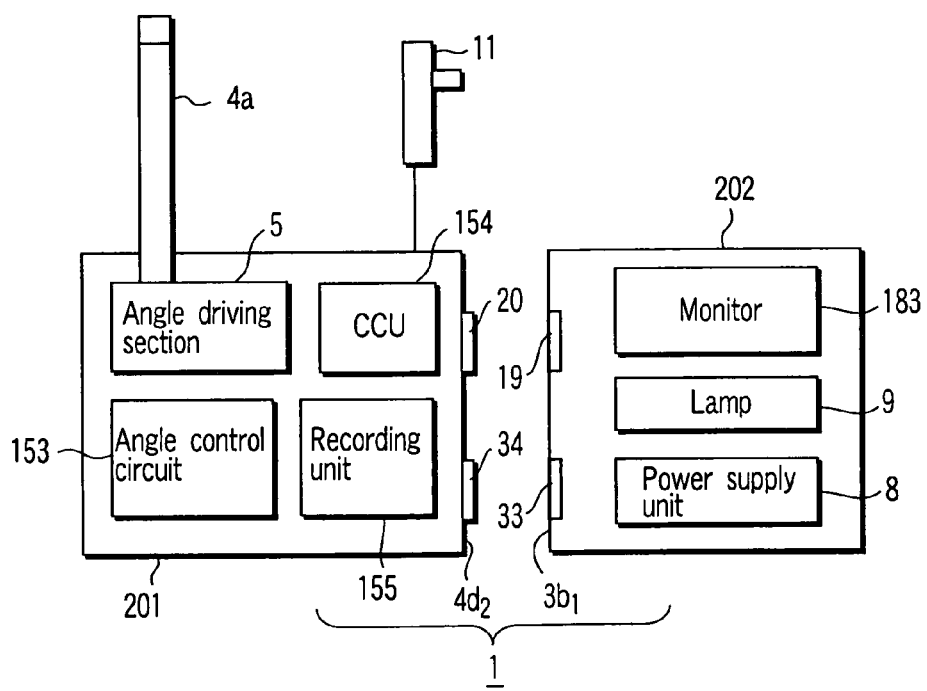
FIG. 40 is a diagram showing a fifth modification example in the endoscope apparatus of the sixth embodiment.

FIG. 40 shows a fifth modification example of the sixth embodiment.

The endoscope apparatus of the present modification example is constituted of a scope unit 201 and fixed unit 202. In this modification example, the monitor 12 of the scope unit 151 in the above-described first modification example is moved as the built-in type monitor 183 in the constitution.

Therefore, in the scope unit 201, the insertion portion 4a, angle driving section 5, angle control circuit 153, camera control unit (CCU) 154, operation remote controller 11, and recording unit 155 are arranged. Moreover, on the end plate 4d2 of the scope unit 151, the LG connector 20 and connector 34 are disposed.

On the other hand, in the fixed unit 202, the lamp 9, power supply unit 8, and monitor 183 are arranged. Moreover, on the scope unit connection surface 3b1, the light source side optical connector 19 and connector 33 are disposed.

By this constitution, the relatively enlarged constituting portion in the apparatus is contained on the fixed unit side, the constituting components having the specifications in accordance with the use purpose are combined, a necessary minimum function is held, and the whole endoscope apparatus can be miniaturized.

Figure 41:
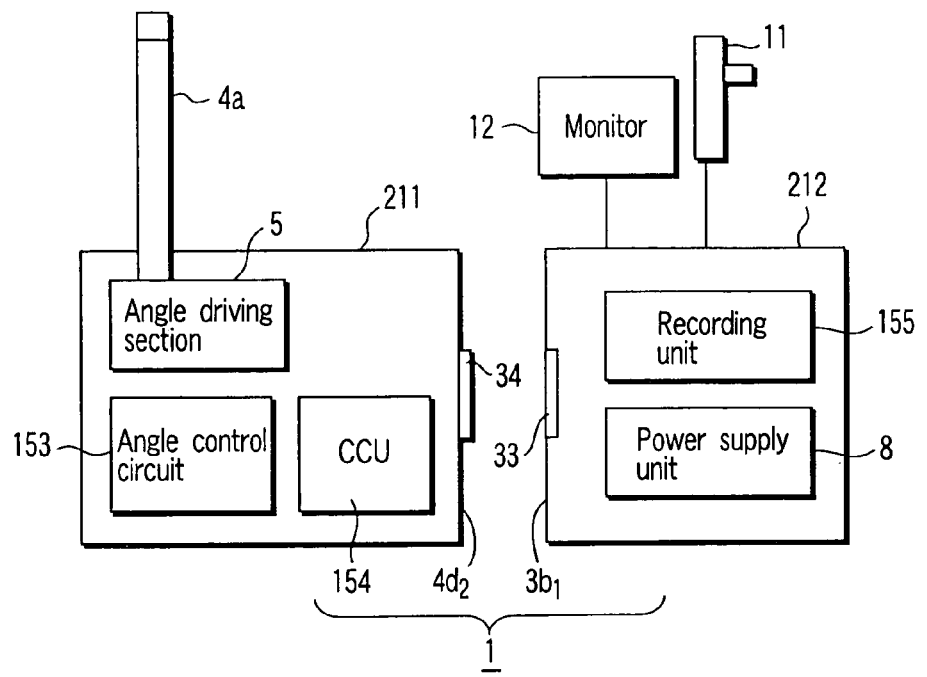
FIG. 41 is a diagram showing a sixth modification example in the endoscope apparatus of the sixth embodiment.

FIG. 41 shows a sixth modification example of the sixth embodiment.

The endoscope apparatus of the present modification example is constituted of a scope unit 211 and fixed unit 212. In the endoscope apparatus of the above-described sixth embodiment, the lamp has been used as the light source for use in the insertion portion 4a, but in this modification example, the light emitting diode (LED) is disposed in the tip end of the insertion portion 4a instead of the lamp (see FIG. 25).

In the scope unit 211, an insertion portion 4a', angle driving section 5, angle control circuit 153, and camera control unit (CCU) 154 are arranged. Only the connector 34 is disposed on the end plate 4d2 of the scope unit 211. On the other hand, in the fixed unit 212, the power supply unit 8, operation remote controller 11, recording unit 155, and monitor 12 are arranged. Moreover, only the connector 33 is disposed on the scope unit connection surface 3b1.

Therefore, in this modification example, in addition to the effect by the sixth embodiment, the miniaturization and power consumption reduction of the apparatus are realized, because LED is used instead of the lamp.

Figure 42:
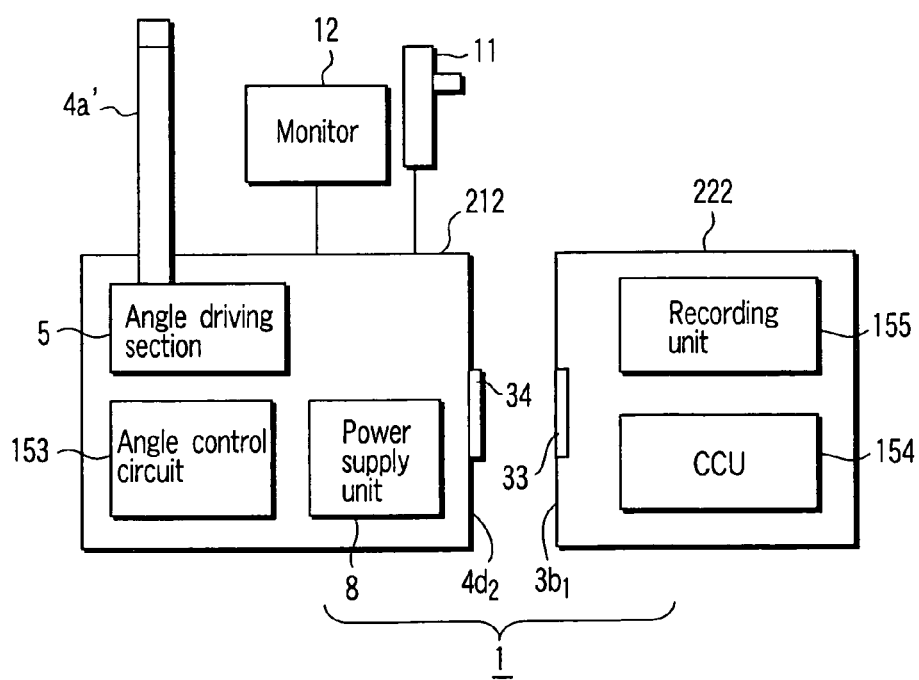
FIG. 42 is a diagram showing a seventh modification example in the endoscope apparatus of the sixth embodiment.

FIG. 42 shows a seventh modification example of the sixth embodiment.

In this modification example, the light emitting diode (LED) is disposed in the tip end of the insertion portion 4a instead of the lamp for use in the above-described second modification example.

Therefore, a fixed unit 222 is equivalent to the fixed unit 172. On the other hand, in a scope unit 221, the insertion portion 4a', angle driving section 5, angle control circuit 153, power supply unit 8, operation remote controller 11, and LCD monitor 12 are arranged.

In this modification example, in addition to the effect of the second modification example, the miniaturization and power consumption reduction of the apparatus are realized, because LED is used instead of the lamp.

Figure 43:
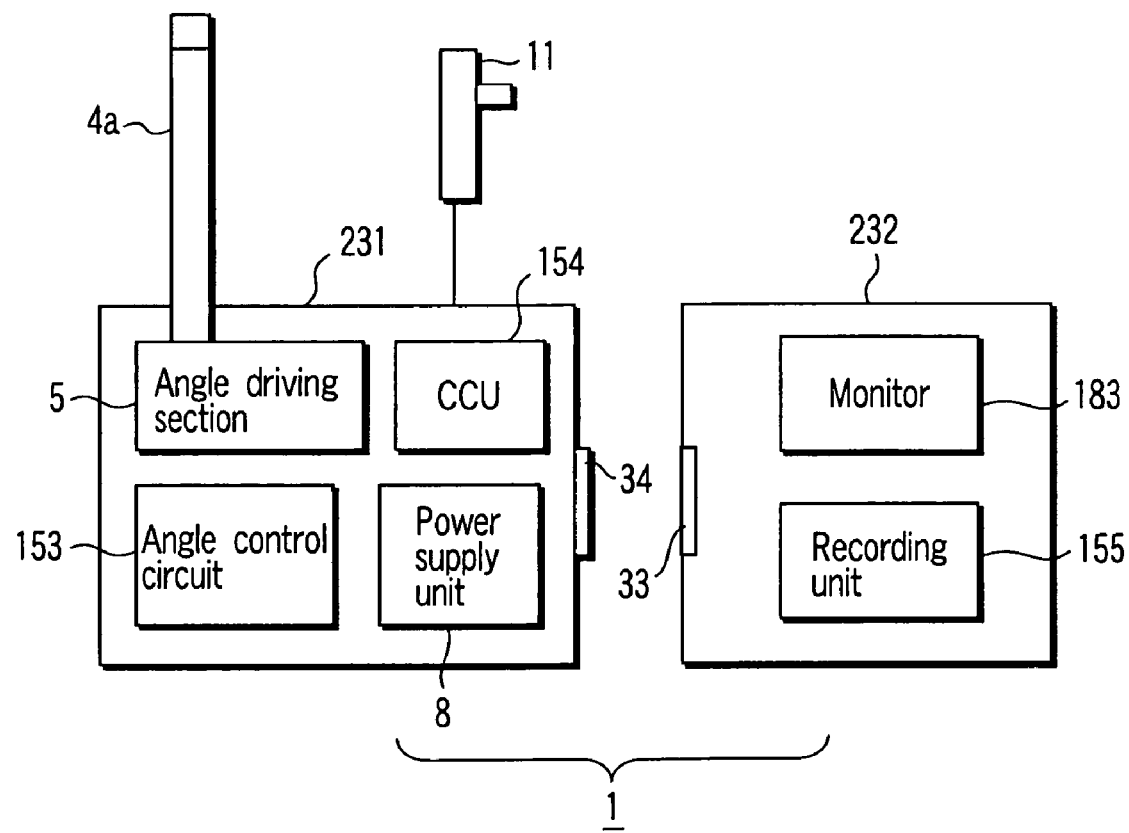
FIG. 43 is a diagram showing an eighth modification example in the endoscope apparatus of the sixth embodiment.

FIG. 43 shows an eighth modification of the sixth embodiment.

In this modification example, the light emitting diode (LED) is disposed in the tip end of the insertion portion 4a instead of the lamp for use in the above-described third modification example.

Therefore, a fixed unit 232 is equivalent to the fixed unit 182. On the other hand, in a scope unit 231, the insertion portion 4a', angle driving section 5, angle control circuit 153, power supply unit 8, and operation remote controller 11 are arranged.

In this modification example, in addition to the effect of the third modification example, the miniaturization and power consumption reduction of the apparatus are realized, because LED is used instead of the lamp.

As described above, in the sixth embodiment and the modification example, the fixed unit and scope unit including the specifications in accordance with the use purpose are prepared. Accordingly, when the units are selected and combined at the use time, the miniaturization, weight reduction, and power consumption reduction can be realized, and further the upgrading can easily be carried out.

Furthermore, needless to say, the present invention can additionally variously be modified/carried out without departing from the scope.

The following effect can be obtained by the above-described embodiments.

Either one of the scope unit side connector and fixed unit side connector disposed in the detachable portion of the base unit and fixed unit is the fixed connector, and the other is the movable connector including the play portion constituting the backlash. Since this axial alignment means is disposed, easy and secure connection is possible concerning the unit change.

The axial alignment means including the scope unit side connector and fixed unit side connector disposed in the detachable portion of the base unit and fixed unit, which are both movable connectors including the play portions constituting the backlashes, is disposed, and therefore the easy and secure connection is possible concerning the unit change.

When the connector on the fixed unit side is connected to that on the base unit side, a connecting position of the fixed unit side to the base unit side can be determined by positioning means of the detachable portion of the base unit of the scope unit and the fixed unit.

When the tapered fitting hole portion of the receiving member of at least either one of the base unit and fixed unit is fitted with the protrusion of the other, the connecting position of the fixed unit side to the base unit side can be determined.

By the axial alignment means of at least either one of the optical connector portion and the connector portion, the fixed connector can axially be aligned with the movable connector.

By the axial alignment means of the connector portion for the electric connection, the fixed connector can axially be aligned with the movable connector.

For the connection detection means of the connector portion, some of a plurality of connector pins disposed on the connector main body can be used to detect the connection of the scope unit.

The base unit of any one of a plurality of different types of scope units disposed beforehand is selectively and detachably connected to the fixed unit, the type and individual piece of the scope unit are identified in accordance with the scope information for the measurement stored in the first control circuit of the base unit, and the measurement function of the endoscope apparatus can be controlled by the first control circuit of the base unit and the second control circuit of the fixed unit.

In accordance with the use purpose, a plurality of types of constituting members mounted on the fixed unit and scope unit are prepared beforehand by various specifications or combinations, accordingly the members are appropriately selected to form an optimum combination at the use time, the miniaturization, weight reduction, and power consumption reduction of the endoscope apparatus can be realized, and further the upgrading can easily be carried out.

What is claimed is:

1. An endoscope apparatus comprising:
   a scope unit including:
   an insertion portion to be inserted in an inspection object space,
   an observation unit for observation disposed in a tip end of the insertion portion, a curved portion which bends the tip end of the insertion portion in an arbitrary direction, and
   a base unit connected to a base end of the insertion portion; and
   a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and
   the detachable portion includes a positioning section for performing positioning which enables the connector on the side of the fixed connector and the connector on the side of the base unit to be connected to each other,
   wherein the scope unit includes an angle driving section which bends the curved portion, and
   wherein the fixed unit includes a lamp which supplies light to the insertion portion, a power supply unit, a monitor in which a photographed image is displayed, an operation remote controller which operates each constituting portion disposed in the scope unit, and a recording unit which records photographed image data or information on the image data, the scope unit further comprising an angle control circuit which controls the angle driving section, and a camera control unit which controls the observation unit.

2. The endoscope apparatus according to claim 1, wherein the positioning section includes a convex portion disposed on either one of the base unit and the fixed unit, and a concave portion disposed in the other to fit with the convex portion.

3. The endoscope apparatus according to claim 1, wherein the positioning section includes a receiving member including a tapered fitting hole portion in at least either one of the base unit and the fixed unit, and a protrusion which is to fit into the fitting hole portion of the receiving member in the other.

4. The endoscope apparatus according to claim 1, wherein the positioning section includes a rail-shaped convex portion in either one of the base unit and the fixed unit, and a concave portion which is to fit with the convex portion in the other, and slides to position the units.

5. The endoscope apparatus according to claim 1, wherein the connector portion includes connection detection means for using some of a plurality of connector pins disposed on a connector main body to detect connection of the scope unit.

6. The endoscope apparatus according to claim 1, wherein a plurality of different types of scope units, which are selectively usable as the scope unit, are prepared, and a selected one of the different types of scope units is detachably connected to the fixed unit, the base unit includes a first control circuit, and the fixed unit includes a second control circuit, the first control circuit stores scope information for measurement to identify a type and individual piece of the scope unit, and the second control circuit includes scope information read means for reading the scope information.

7. An endoscope apparatus comprising:
a scope unit including:
an insertion portion to be inserted in an inspection object space,
an observation unit for observation disposed in a tip end of the insertion portion, a curved portion which bends the tip end of the insertion portion in an arbitrary direction, and
a base unit connected to a base end of the insertion portion; and
a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and
the detachable portion includes a positioning section for performing positioning which enables the connector on the side of the fixed connector and the connector on the side of the base unit to be connected to each other,
wherein the scope unit includes an angle driving section which bends the curved portion, and
wherein the fixed unit includes a lamp which supplies light to the insertion portion, and a power supply unit, and the scope unit includes an angle control circuit which controls the angle driving section, a camera control unit which controls the observation unit, a monitor in which a photographed image is displayed, an operation remote controller which operates each constituting portion disposed in the scope unit, and a recording unit which records photographed image data or information on the image data.

8. An endoscope apparatus comprising:
a scope unit including:
an insertion portion to be inserted in an inspection object space,
an observation unit for observation disposed in a tip end of the insertion portion, a curved portion which bends the tip end of the insertion portion in an arbitrary direction, and
a base unit connected to a base end of the insertion portion; and
a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and
the detachable portion includes a positioning section for performing positioning which enables the connector on the side of the fixed connector and the connector on the side of the base unit to be connected to each other,
wherein the scope unit includes an angle driving section which bends the curved portion, and
wherein the fixed unit includes a camera control unit which controls the observation unit, and a recording unit which records photographed image data or information on the image data, and the scope unit includes an angle control circuit which controls the angle driving section, a lamp which supplies light to the insertion portion, a power supply unit, a monitor in which a photographed image is displayed, and an operation remote controller which operates each constituting portion disposed in the scope unit.

9. An endoscope apparatus comprising:
a scope unit including:
an insertion portion to be inserted in an inspection object space,
an observation unit for observation disposed in a tip end of the insertion portion, a curved portion which bends the tip end of the insertion portion in an arbitrary direction, and
a base unit connected to a base end of the insertion portion; and
a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and
the detachable portion includes a positioning section for performing positioning which enables the connector on the side of the fixed connector and the connector on the side of the base unit to be connected to each other,
wherein the scope unit includes an angle driving section which bends the curved portion, and
wherein the fixed unit includes a built-in type monitor disposed in the fixed unit, a recording unit which records photographed image data or information on the image data, a power supply unit, and an operation remote controller which operates each constituting portion disposed in the scope unit, and the scope unit includes an angle control circuit which controls the angle driving section, a lamp which supplies light to the insertion portion, and a camera control unit which controls the observation unit.

10. An endoscope apparatus comprising:
a scope unit including:

an insertion portion to be inserted in an inspection object space, an observation unit for observation disposed in a tip end of the insertion portion, a curved portion which bends the tip end of the insertion portion in an arbitrary direction, and a base unit connected to a base end of the insertion portion; and a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and the detachable portion includes a positioning section for performing positioning which enables the connector on the side of the fixed connector and the connector on the side of the base unit to be connected to each other, wherein the scope unit includes an angle driving section which bends the curved portion, and wherein the fixed unit includes a lamp which supplies light to the insertion portion, a power supply unit, and a built-in type monitor disposed in the fixed unit, and the scope unit includes an angle control circuit which controls the angle driving section, a camera control unit which controls the observation unit, a recording unit which records photographed image data or information on the image data, and an operation remote controller which operates each constituting portion disposed in the scope unit.

11. An endoscope apparatus comprising:

a scope unit including:

an insertion portion to be inserted in an inspection object space, an observation unit for observation disposed in a tip end of the insertion portion, a curved portion which bends the tip end of the insertion portion in an arbitrary direction, and a base unit connected to a base end of the insertion portion; and a fixed unit to which the base unit is detachably connected, wherein at least one of a connector on the side of the base unit and a connector on the side of the fixed unit in a connector portion disposed in a detachable portion of the base unit and the fixed unit is a movable connector, which is movable in a direction perpendicular to an axial direction of the movable connector, and the detachable portion includes a positioning section for performing positioning which enables the connector on the side of the fixed connector and the connector on the side of the base unit to be connected to each other, wherein the scope unit includes an angle driving section which bends the curved portion, and wherein the fixed unit includes a recording unit which records photographed image data or information on the image data, a power supply unit, a monitor in which a photographed image is displayed, and an operation remote controller which operates each constituting portion disposed in the scope unit, and the insertion portion includes an illuminating portion constituted of a light emitting diode (LED) in a tip end, an angle control circuit which controls the angle driving section, and a camera control unit which controls the observation unit.

12. The endoscope apparatus according to claim 11 wherein the positioning section includes a convex portion disposed on either one of the base unit and the fixed unit, and a concave portion disposed in the other to fit with the convex portion.

13. The endoscope apparatus according to claim 11 wherein the positioning section includes a receiving member including a tapered fitting hole portion in at least either one of the base unit and the fixed unit, and a protrusion which is to fit into the fitting hole portion of the receiving member in the other.

14. The endoscope apparatus according to claim 11 wherein the positioning section includes a rail-shaped convex portion in either one of the base unit and the fixed unit, and a concave portion which is to fit with the convex portion in the other, and slides to position the units.

15. The endoscope apparatus according to claim 11 wherein the connector portion includes connection detection means for using some of a plurality of connector pins disposed on a connector main body to detect connection of the scope unit.

16. The endoscope apparatus according to claim 11 wherein a plurality of different types of scope units, which are selectively usable as the scope unit, are prepared, and a selected one of the different types of scope units is detachably connected to the fixed unit, the base unit includes a first control circuit, and the fixed unit includes a second control circuit, the first control circuit stores scope information for measurement to identify a type and individual piece of the scope unit, and the second control circuit includes scope information read means for reading the scope information.

* * * * *